US011874273B2

(12) United States Patent
Bruenn et al.

(10) Patent No.: US 11,874,273 B2
(45) Date of Patent: Jan. 16, 2024

(54) MEANS AND METHODS FOR THE DETERMINATION OF THE BIOLOGICAL ACTIVITY OF BONT/E IN CELLS

(71) Applicant: MERZ PHARMA GMBH & CO. KGAA, Frankfurt am Main (DE)

(72) Inventors: Cornelia Bruenn, Frankfurt (DE); Gerd Mander, Frankfurt (DE)

(73) Assignee: MERZ PHARMA GMBH & CO. KGAA

( * ) Notice: Subject to any disclaimer, the term of this patent is extended or adjusted under 35 U.S.C. 154(b) by 386 days.

(21) Appl. No.: 17/122,054

(22) Filed: Dec. 15, 2020

(65) Prior Publication Data

US 2021/0116440 A1 Apr. 22, 2021

Related U.S. Application Data

(62) Division of application No. 15/536,839, filed as application No. PCT/EP2015/080395 on Dec. 18, 2015, now Pat. No. 10,900,955.

(30) Foreign Application Priority Data

Dec. 19, 2014 (EP) .................................... 14199282

(51) Int. Cl.
*G01N 33/50* (2006.01)
*C07K 16/18* (2006.01)
(Continued)

(52) U.S. Cl.
CPC ..... *G01N 33/5014* (2013.01); *C07K 16/1282* (2013.01); *C07K 16/18* (2013.01);
(Continued)

(58) Field of Classification Search
CPC ..................................................... C07K 16/18
See application file for complete search history.

(56) References Cited

U.S. PATENT DOCUMENTS 7,691,983 B2 4/2010 Fernandez-Salas et al.
8,936,915 B2 1/2015 Bavari et al.
(Continued)

FOREIGN PATENT DOCUMENTS

EP 1926744 B1 4/2010
JP H10504801 A 5/1998
(Continued)

OTHER PUBLICATIONS

Jones et al. Development of improved SNAP25 endopeptidase immunoassay for botulinum type A and E toxins. Journal of Immunological Methods. 329 (1-2): 92-101 (Oct. 23, 2007).*
(Continued)

*Primary Examiner* — Gailene Gabel
(74) *Attorney, Agent, or Firm* — RAPHAEL BELLUM PLLC

(57) ABSTRACT

The present invention pertains to a polyclonal or monoclonal antibody specifically binding to BoNT/E-cleaved SNAP-25. Further, the invention provides a method for directly determining the biological activity of BoNT/E in cells, comprising the steps of: a) incubating cells susceptible to BoNT/E intoxication with BoNT/E for a time and under conditions which allow for the BoNT/E to exert its biological activity; b) fixing the cells and, optionally, permeabilizing the cells with a detergent; c) contacting the cells with at least a first capture antibody specifically binding to non-cleaved and BoNT/E-cleaved SNAP-25, and with at least a second capture antibody specifically binding to BoNT/E-cleaved SNAP-25, wherein the second capture antibody is an antibody of the invention, under conditions which allow for binding of said capture antibodies to the indicated substrates; d) contacting the cells with at least a first detection antibody specifically binding to the first capture antibody, under conditions which allow for binding of said first
(Continued)

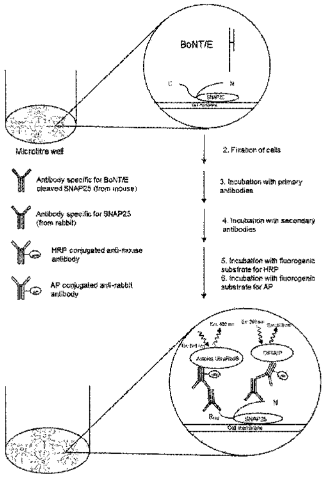

detection antibody to said first capture antibody, thus forming first detection complexes, and with at least a second detection antibody specifically binding to the second capture antibody, under conditions which allow for binding of said second detection antibody to said second capture antibody, thus forming second detection complexes, and wherein the first detection antibody is different from the second detection antibody; e) determining the amount of the first and second detection complexes of step d); and f) calculating the amount of SNAP-25 cleaved by BoNT/E in said cells by means of the second detection complexes, thereby determining the biological activity of BoNT/E in said cells. Furthermore, the invention relates to a kit for carrying out the method of the invention.

4 Claims, 1 Drawing Sheet

Specification includes a Sequence Listing.

(51) Int. Cl.
*C07K 16/12* (2006.01)
*G01N 33/573* (2006.01)

(52) U.S. Cl.
CPC ....... *G01N 33/573* (2013.01); *C07K 2317/34* (2013.01); *G01N 2333/33* (2013.01); *G01N 2333/952* (2013.01); *G01N 2800/709* (2013.01)

(56) References Cited

U.S. PATENT DOCUMENTS

| | | | |
|---|---|---|---|
| 9,809,809 B2 | 11/2017 | Schmidt et al. | |
| 2005/0100973 A1 | 5/2005 | Steward et al. | |
| 2009/0247609 A1 | 10/2009 | Kaufmann et al. | |
| 2010/0216181 A1 | 8/2010 | Daigh et al. | |
| 2010/0279403 A1 | 11/2010 | Rajesh et al. | |
| 2012/0225436 A1* | 9/2012 | Fernandez-Salas | G01N 33/566 435/7.1 |
| 2015/0064747 A1 | 3/2015 | Gouda et al. | |

FOREIGN PATENT DOCUMENTS

| | | | |
|---|---|---|---|
| WO | 95/32738 | A1 | 12/1995 |
| WO | 95/33850 | A1 | 12/1995 |
| WO | 00/12728 | A1 | 3/2000 |
| WO | 01/14570 | A1 | 3/2001 |
| WO | 2005/007185 | A2 | 1/2005 |
| WO | 2005/068494 | A2 | 7/2005 |
| WO | 2006/017749 | A2 | 2/2006 |
| WO | 2006/020208 | A2 | 2/2006 |
| WO | 2006/076902 | A2 | 7/2006 |
| WO | 2006/107921 | A2 | 10/2006 |
| WO | 2009/114748 | A1 | 9/2009 |
| WO | 2010/105234 | A1 | 9/2010 |
| WO | 2011/025852 | A1 | 3/2011 |
| WO | 2011/056971 | A2 | 5/2011 |
| WO | 2012/135621 | A2 | 10/2012 |
| WO | 2013/068476 | A1 | 5/2013 |
| WO | 2013/091895 | A1 | 6/2013 |
| WO | 2014/207109 | A1 | 12/2014 |

OTHER PUBLICATIONS

Altschul et al., "Basic Local Alignment Search Tool", J. Mol. Biol. 1990, 215, 403-410.

Armbruster and Pry "Limit of Blank, Limit of Detection and Limit of Quantitation", Rev. 2008, 29 (Supplement 1): S49-S52.

Arnon et al., "Botulinum Toxin as a Biological Weapon Medical and Public Health Management", JAMA, 2001, vol. 285, No. 8, 1059-1070.

Chotia et al., "Conformations of immunoglobulin hypervariable regions", Nature, 1989, 342(6252), 877-883.

Couesnon et al., "Expression of botulinum neurotoxins A and E, and associated non-toxin genes, during the transition phase and stability at high temperature: analysis by quantitative reverse transcription-PCR", Microbiology, 2006, 152, 759-770.

Dressler et al., "Mouse Diaphragm Assay for Detection of Antibodies Against Botulinum Toxin Type B", Mov. Disord. 2005, 20:1617-1619.

Galfre and Milstein "[1] Preparation of Monoclonal Antibodies: Strategies and Procedures", Methods in Enzymology, 1981, vol. 73, 3-46.

Gee et al., "Fluorogenic Substrates Based on Fluorinated Umbelliferones for Continuous Assays of Phosphatases and beta-Galactosidases", Analytical Biochemistry, 1999, 273, 41-48.

Higgins and Sharp "Fast and sensitive multiple sequence alignments on a microcomputer", Cabios Communications, 1989, vol. 5, No. 2, 151-153.

Jost et al., "Botulinum Neurotoxin Type A Free of Complexing Proteins (XEOMIN) in Focal Dystonia", Drugs, 2007, 67 (5): 669-683.

Keller "Recovery from Botulinum Neurotoxin Poisoning in Vivo", Neuroscience, 2006, 139, 629-637.

Kohler and Milstein "Continuous cultures of fused cells secreting antibody of predefined specificity", Nature, 1975, vol. 256, 495-497.

Krieglstein et al., "Arrangement of disulfide bridges and positions of sulfhydryl groups in tetanus toxin", Eur. J. Biochem., (1990), 188, 39-45.

Krieglstein et al., "Limited proteolysis of tetanus toxin", Eur. J. Biochem., (1991), 202, 41-51.

Krieglstein et al., "Covalent Structure of Botulinum Neurotoxin Type A: Location of Sulfhydryl Groups, and Disulfide Bridges and Identification of C-Termini of Light and Heavy Chains", J. Protein Chem., (1994), vol. 13, No. 1, 49-57.

Malmborg and Borrebaeck "BIAcore as a tool in antibody engineering", J. Immunol. Methods, 1995, 183, 7-13.

Saul B. Needleman and Christian D. Wunsch "A General Method Applicable to the Search for Similarities in the Amino Acid Sequence of Two Proteins", J. Mol. Bio., (1970), 48, 443-453.

Pearce et al., "Measurement of Botulinum Toxin Activity: Evaluation of the Lethality Assay", Toxicol. Appl. Pharmacol., (1994), 128, 69-77.

Pellett et al., "Sensitive and quantitative detection of botulinum neurotoxin in neurons derived from mouse embryonic stem cells", Biochem. Biophys. Res. Commun. 2011, 404(1): 388-392.

Plueckthun "The Pharmacology of Monoclonal Antibodies", 1994, vol. 113, Rosenberg and Moore Eds., Springer-Verlag, New York, 269-315.

Sambrook "Molecular Cloning: A Laboratory Manual", Cold Spring Harbor Laboratory, third edition, 2001, Detection Systems, pp. A9.1-A9-49.

Stephen Silberstein "Botulinum Neurotoxins: Origins and Basic Mechanisms of Action", Pain Practice, 2004, vol. 4, Issue 1S, S19-S26.

Temple F. Smith "Comparison of Biosequences", Adv. Appl. Math. 2 (1981), 482-489.

Donald W. Straughan "Progress in Applying the Three Rs to the Potency Testing of Botulinum Toxin Type A", ATLA 34, (2006), 305-313.

Tuuminen et al., "3-p-Hydroxyphenylpropionic Acid—A Sensitive Fluorogenic Substrate for Automated Fluorometric Enzyme Immunoassays", J. Immunoassay, 1991, 12(1), 29-46.

Whitemarsh et al., "Novel Application of Human Neurons Derived from Induced Pluripotent Stem Cells for Highly Sensitive Botulinum Neurotoxin Detection", Toxicol. Sci., (2012), 126(2), 426-435.

Yu et al., "Human Induced Pluripotent Stem Cells Free of Vector and Transgene Sequences", Science, 2009, 324(5928): 797-801.

International Preliminary Report on Patentability in International Application No. PCT/EP2015/080395, dated Jun. 29, 2017.

(56) References Cited

OTHER PUBLICATIONS

Fernandez-Salas et al., "Botulinum Neurotoxin Serotype a Specific Cell-Based Potency Assay to Replace the Mouse Bioassay", PLOS One, Nov. 2012, vol. 7, Issue 11, e49516.
Jones et al., "Development of improved SNAP25 endopeptides immuno-assays for botulinim type A and E toxins", Journal of Immunoligical Methods, 329, (2008), pp. 92-101.
Hoffman et al., "A High-Throughput, Cell-Based screening Method for siRNA and Small Molecule Inhibitors of mTORC1 Signaling Using the In Cell Western Technique", ASSAY and Drug Development Technologies, 2010, pp. 186-199.
Mander et al., "Potency Assay for Botulinium Neurotoxin Type A based on Neuronal Cells as a Replacement for the Mouse BioAssay", Abstract, Toxicon, 2014, vol. 93, Supp. pp. S41-S42.
Roberts et al., "A comparison of the sensitivity and specificity of enzyme immunoassays and time-resolved flouroimmunoassay", J. Immunol. Methods, 1991, vol. 143, pp. 49-56.

* cited by examiner

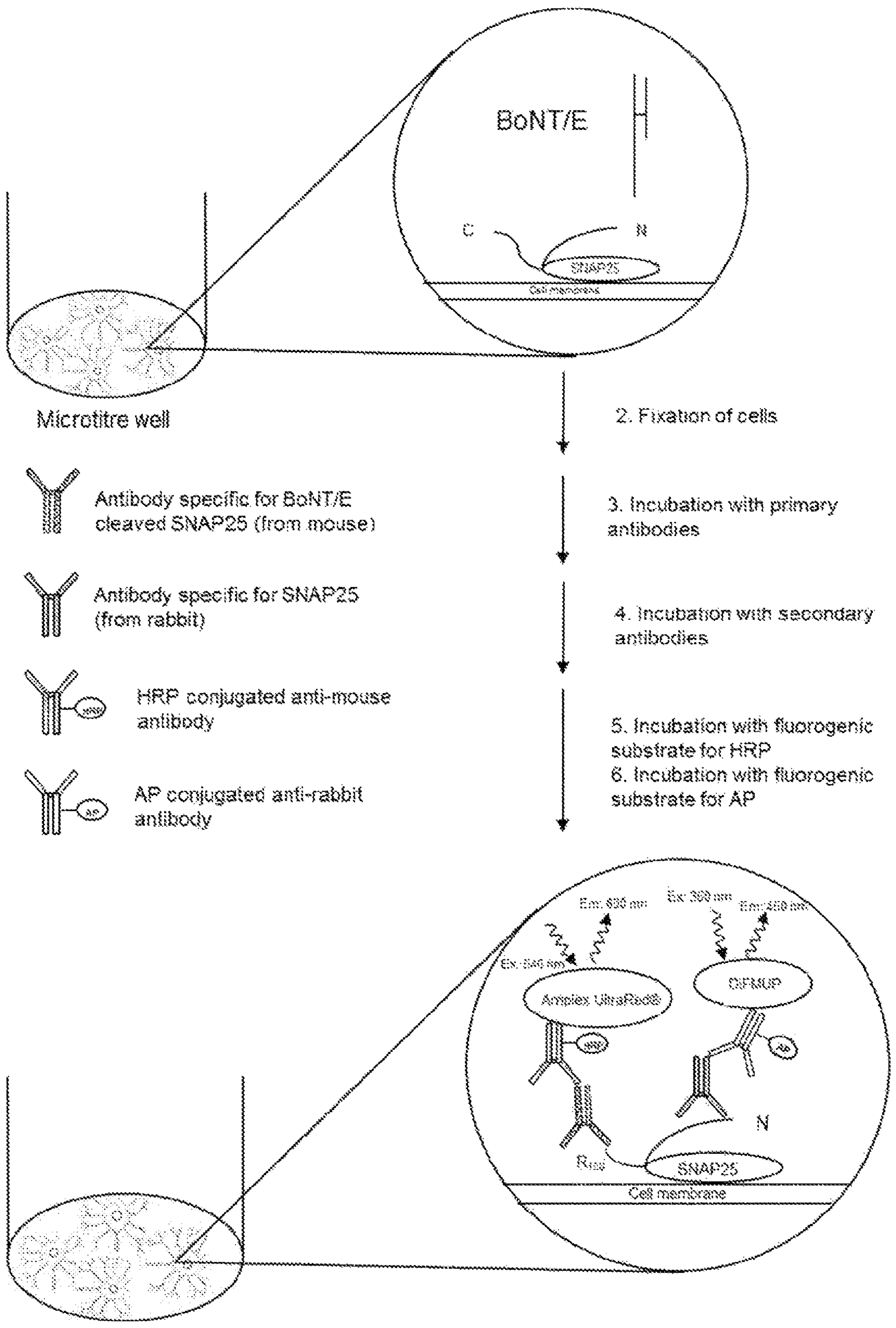
BoNT/E
C
N
SNAP25
Cell membrane
Microtitre well
2. Fixation of cells
Antibody specific for BoNT/E cleaved SNAP25 (from mouse)
3. Incubation with primary antibodies
Antibody specific for SNAP25 (from rabbit)
4. Incubation with secondary antibodies
HRP conjugated anti-mouse antibody
5. Incubation with fluorogenic substrate for HRP
6. Incubation with fluorogenic substrate for AP
AP conjugated anti-rabbit antibody
Amplex UltraRed®
DiFMUP
N
SNAP25
Cell membrane

SEQUENCE LISTING

```
<160> NUMBER OF SEQ ID NOS: 22

<210> SEQ ID NO 1
<211> LENGTH: 13
<212> TYPE: PRT
<213> ORGANISM: Artificial
<220> FEATURE:
<223> OTHER INFORMATION: BoNT/E epitope

<400> SEQUENCE: 1

Cys Asn Glu Ile Asp Thr Gln Asn Arg Gln Ile Asp Arg
1               5                   10


<210> SEQ ID NO 2
<211> LENGTH: 12
<212> TYPE: PRT
<213> ORGANISM: Homo sapiens

<400> SEQUENCE: 2
```

-continued

```
Asn Glu Ile Asp Thr Gln Asn Arg Gln Ile Asp Arg
1               5                   10


<210> SEQ ID NO 3
<211> LENGTH: 11
<212> TYPE: PRT
<213> ORGANISM: Homo sapiens

<400> SEQUENCE: 3

Glu Ile Asp Thr Gln Asn Arg Gln Ile Asp Arg
1               5                   10


<210> SEQ ID NO 4
<211> LENGTH: 10
<212> TYPE: PRT
<213> ORGANISM: Homo sapiens

<400> SEQUENCE: 4

Ile Asp Thr Gln Asn Arg Gln Ile Asp Arg
1               5                   10


<210> SEQ ID NO 5
<211> LENGTH: 9
<212> TYPE: PRT
<213> ORGANISM: Homo sapiens

<400> SEQUENCE: 5

Asp Thr Gln Asn Arg Gln Ile Asp Arg
1               5


<210> SEQ ID NO 6
<211> LENGTH: 8
<212> TYPE: PRT
<213> ORGANISM: Homo sapiens

<400> SEQUENCE: 6

Thr Gln Asn Arg Gln Ile Asp Arg
1               5


<210> SEQ ID NO 7
<211> LENGTH: 7
<212> TYPE: PRT
<213> ORGANISM: Homo sapiens

<400> SEQUENCE: 7

Gln Asn Arg Gln Ile Asp Arg
1               5


<210> SEQ ID NO 8
<211> LENGTH: 6
<212> TYPE: PRT
<213> ORGANISM: Homo sapiens

<400> SEQUENCE: 8

Asn Arg Gln Ile Asp Arg
1               5


<210> SEQ ID NO 9
<211> LENGTH: 3756
<212> TYPE: DNA
<213> ORGANISM: Clostridium botulinum

<400> SEQUENCE: 9

atgccaaaaa ttaatagttt taattataat gatcctgtta atgatagaac aattttatat     60
```

-continued

```
attaaaccag gcggttgtca agaattttat aaatcattta atattatgaa aaatatttgg    120
ataattccag agagaaatgt aattggtaca accccccaag attttcatcc gcctacttca    180
ttaaaaaatg gagatagtag ttattatgac cctaattatt tacaaagtga tgaagaaaag    240
gatagatttt taaaaatagt cacaaaaata tttaatagaa taaataataa tctttcagga    300
gggattttat tagaagaact gtcaaaagct aatccatatt tagggaatga taatactcca    360
gataatcaat tccatattgg tgatgcatca gcagttgaga ttaaattctc aaatggtagc    420
caagacatac tattacctaa tgttattata atgggagcag agcctgattt atttgaaact    480
aacagttcca atatttctct aagaaataat tatatgccaa gcaatcaccg ttttggatca    540
atagctatag taacattctc acctgaatat tcttttagat ttaatgataa ttgtatgaat    600
gaatttattc aagatcctgc tcttacatta atgcatgaat taatacattc attacatgga    660
ctatatgggg ctaaagggat tactacaaag tatactataa cacaaaaaca aaatccccta    720
ataacaaata taagaggtac aaatattgaa gaattcttaa cttttggagg tactgattta    780
aacattatta ctagtgctca gtccaatgat atctatacta atcttctagc tgattataaa    840
aaaatagcgt ctaaacttag caaagtacaa gtatctaatc cactacttaa tccttataaa    900
gatgtttttg aagcaaagta tggattagat aaagatgcta gcggaattta ttcggtaaat    960
ataaacaaat ttaatgatat ttttaaaaaa ttatacagct ttacggaatt tgatttacga   1020
actaaatttc aagttaaatg taggcaaact tatattggac agtataaata cttcaaactt   1080
tcaaacttgt taaatgattc tatttataat atatcagaag gctataatat aaataattta   1140
aaggtaaatt ttagaggaca gaatgcaaat ttaaatccta gaattattac accaattaca   1200
ggtagaggac tagtaaaaaa aatcattaga ttttgtaaaa atattgtttc tgtaaaaggc   1260
ataaggaaat caatatgtat cgaaataaat aatggtgagt tattttttgt ggcttccgag   1320
aatagttata atgatgataa tataaatact cctaaagaaa ttgacgatac agtaacttca   1380
aataataatt atgaaaatga tttagatcag gttattttaa attttaatag tgaatcagca   1440
cctggacttt cagatgaaaa attaaattta actatccaaa atgatgctta tataccaaaa   1500
tatgattcta atggaacaag tgatatagaa caacatgatg ttaatgaact taatgtattt   1560
ttctatttag atgcacagaa agtgcccgaa ggtgaaaata atgtcaatct cacctcttca   1620
attgatacag cattattaga acaacctaaa atatatacat ttttttcatc agaatttatt   1680
aataatgtca ataaacctgt gcaagcagca ttatttgtaa gctggataca acaagtgtta   1740
gtagatttta ctactgaagc taaccaaaaa agtactgttg ataaaattgc agatatttct   1800
atagttgttc catatatagg tcttgcttta aatataggaa atgaagcaca aaaaggaaat   1860
tttaaagatg cacttgaatt attaggagca ggtattttat tagaatttga acccgagctt   1920
ttaattccta caattttagt attcacgata aaatcttttt taggttcatc tgataataaa   1980
aataaagtta ttaaagcaat aaataatgca ttgaaagaaa gagatgaaaa atggaaagaa   2040
gtatatagtt ttatagtatc gaattggatg actaaaatta atacacaatt taataaaaga   2100
aaagaacaaa tgtatcaagc tttacaaaat caagtaaatg caattaaaac aataatagaa   2160
tctaagtata atagttatac tttagaggaa aaaaatgagc ttacaaataa atatgatatt   2220
aagcaaatag aaaatgaact taatcaaaag gtttctatag caatgaataa tatagacagg   2280
ttcttaactg aaagttctat atcctattta atgaaaataa taaatgaagt aaaaattaat   2340
aaattaagag aatatgatga gaatgtcaaa acgtatttat tgaattatat tatacaacat   2400
ggatcaatct tgggagagag tcagcaagaa ctaaattcta tggtaactga taccctaaat   2460
```

-continued

```
aatagtattc cttttaagct ttcttcttat acagatgata aaattttaat ttcatatttt   2520

aataaattct ttaagagaat taaaagtagt tcagttttaa atatgagata taaaaatgat   2580

aaatacgtag atacttcagg atatgattca aatataaata ttaatggaga tgtatataaa   2640

tatccaacta ataaaaatca atttggaata tataatgata aacttagtga agttaatata   2700

tctcaaaatg attacattat atatgataat aaatataaaa attttagtat tagtttttgg   2760

gtaagaattc ctaactatga taataagata gtaaatgtta ataatgaata cactataata   2820

aattgtatga gagataataa ttcaggatgg aaagtatctc ttaatcataa tgaaataatt   2880

tggacattcg aagataatcg aggaattaat caaaaattag catttaacta tggtaacgca   2940

aatggtattt ctgattatat aaataagtgg atttttgtaa ctataactaa tgatagatta   3000

ggagattcta aactttatat taatggaaat ttaatagatc aaaaatcaat tttaaattta   3060

ggtaatattc atgttagtga caatatatta tttaaaatag ttaattgtag ttatacaaga   3120

tatattggta ttagatattt taatattttt gataaagaat tagatgaaac agaaattcaa   3180

actttatata gcaatgaacc taatacaaat attttgaagg atttttgggg aaattatttg   3240

ctttatgaca aagaatacta tttattaaat gtgttaaaac caaataactt tattgatagg   3300

agaaaagatt ctactttaag cattaataat ataagaagca ctattctttt agctaataga   3360

ttatatagtg gaataaaagt taaaatacaa agagttaata atagtagtac taacgataat   3420

cttgttagaa agaatgatca ggtatatatt aattttgtag ccagcaaaac tcacttattt   3480

ccattatatg ctgatacagc taccacaaat aaagagaaaa caataaaaat atcatcatct   3540

ggcaatagat ttaatcaagt agtagttatg aattcagtag gaaattgtac aatgaatttt   3600

aaaaataata atggaaataa tattgggttg ttaggtttca aggcagatac tgtcgttgct   3660

agtacttggt attatacaca tatgagagat catacaaaca gcaatggatg tttttggaac   3720

tttatttctg aagaacatgg atggcaagaa aaataa                              3756
```

<210> SEQ ID NO 10
<211> LENGTH: 1251
<212> TYPE: PRT
<213> ORGANISM: Clostridium botulinum

<400> SEQUENCE: 10

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

-continued

```
Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560
```

-continued

```
Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
```

-continued 980 985 990

Val Thr Ile Thr Asn Asp Arg Leu Gly Asp Ser Lys Leu Tyr Ile Asn
995 1000 1005

Gly Asn Leu Ile Asp Gln Lys Ser Ile Leu Asn Leu Gly Asn Ile
1010 1015 1020

His Val Ser Asp Asn Ile Leu Phe Lys Ile Val Asn Cys Ser Tyr
1025 1030 1035

Thr Arg Tyr Ile Gly Ile Arg Tyr Phe Asn Ile Phe Asp Lys Glu
1040 1045 1050

Leu Asp Glu Thr Glu Ile Gln Thr Leu Tyr Ser Asn Glu Pro Asn
1055 1060 1065

Thr Asn Ile Leu Lys Asp Phe Trp Gly Asn Tyr Leu Leu Tyr Asp
1070 1075 1080

Lys Glu Tyr Tyr Leu Leu Asn Val Leu Lys Pro Asn Asn Phe Ile
1085 1090 1095

Asp Arg Arg Lys Asp Ser Thr Leu Ser Ile Asn Asn Ile Arg Ser
1100 1105 1110

Thr Ile Leu Leu Ala Asn Arg Leu Tyr Ser Gly Ile Lys Val Lys
1115 1120 1125

Ile Gln Arg Val Asn Asn Ser Ser Thr Asn Asp Asn Leu Val Arg
1130 1135 1140

Lys Asn Asp Gln Val Tyr Ile Asn Phe Val Ala Ser Lys Thr His
1145 1150 1155

Leu Phe Pro Leu Tyr Ala Asp Thr Ala Thr Thr Asn Lys Glu Lys
1160 1165 1170

Thr Ile Lys Ile Ser Ser Ser Gly Asn Arg Phe Asn Gln Val Val
1175 1180 1185

Val Met Asn Ser Val Gly Asn Cys Thr Met Asn Phe Lys Asn Asn
1190 1195 1200

Asn Gly Asn Asn Ile Gly Leu Leu Gly Phe Lys Ala Asp Thr Val
1205 1210 1215

Val Ala Ser Thr Trp Tyr Tyr Thr His Met Arg Asp His Thr Asn
1220 1225 1230

Ser Asn Gly Cys Phe Trp Asn Phe Ile Ser Glu Glu His Gly Trp
1235 1240 1245

Gln Glu Lys
1250

<210> SEQ ID NO 11
<211> LENGTH: 3819
<212> TYPE: DNA
<213> ORGANISM: Artificial
<220> FEATURE:
<223> OTHER INFORMATION: recombinant protein BONT/E with MDM2 binding motif

<400> SEQUENCE: 11
atgccgaaaa tcaacagctt caactataac gatccggtga acgatcgtac catcctgtat 60
attaaaccgg gcggttgcca ggaattttac aaaagcttca acatcatgaa aaacatctgg 120
attattccgg aacgtaacgt gattggcacc accccgcagg attttcatcc gccgaccagc 180
ctgaaaaacg gcgatagcag ctattatgat ccgaactatc tgcagtctga tgaagaaaaa 240
gatcgcttcc tgaaaatcgt gaccaaaatc ttcaaccgca tcaacaacaa cctgagcggc 300
ggcattctgc tggaagaact gagcaaagcg aatccgtatc tgggcaacga taacactcca 360

-continued

```
gataaccagt ttcatattgg tgatgcgagc gcggtggaaa ttaaatttag caacggctct    420
caggacattc tgctgccgaa cgtgattatt atgggcgcgg aaccggacct gtttgaaacc    480
aacagcagca acattagcct gcgtaacaac tatatgccga gcaaccatgg ttttggcagc    540
attgcgattg tgacctttag cccggaatat agctttcgct tcaacgataa cagcatgaac    600
gaatttattc aggacccggc gctgaccctg atgcacgagc tgattcatag cctgcatggc    660
ctgtatggcg cgaaaggcat taccaccaaa tataccatca cccagaaaca gaatccgctg    720
attaccaaca ttcgtggcac caacattgaa gaatttctga cctttggcgg caccgatctg    780
aacattatta ccagcgcgca gagcaacgat atctatacca acctgctggc cgattataaa    840
aaaatcgcgt ctaaactgag caaagtgcag gtgagcaatc cgctgctgaa tccgtataaa    900
gatgtgtttg aagcgaaata tggcctggat aaagatgcta gcggcattta tagcgtgaac    960
atcaacaaat tcaacgacat cttcaaaaaa ctgtatagct ttaccgaatt tgatctggcc   1020
accaaatttc aggtgaaatg ccgccagacc tatattggcc agtataaata ttttaaactg   1080
agcaacctgc tgaacgatag catttacaac atcagcgaag gctataacat caacaacctg   1140
aaagtgaact ttcgtggcca gaacgcgaat ttaaatccgc gtattattac cccgattacc   1200
ggccgtggac tagtgaaaaa aattatccgt ttttgcgtgc gtggcattat caccagcctg   1260
acctttgaac ataattgggc acagctgacc agcaaaagcc tggtgccgcg tggcagcaaa   1320
gcgttaaatg atttatgcat cgaaatcaac aacggcgaac tgttttttgt ggcgagcgaa   1380
aacagctata acgatgataa catcaacacc ccgaaagaaa ttgatgatac cgtgaccagc   1440
aataacaact acgaaaacga tctggatcag gtgattctga actttaacag cgaaagcgca   1500
ccgggcctgt ctgatgaaaa actgaacctg accattcaga acgatgcgta tatcccgaaa   1560
tatgatagca acggcaccag cgatattgaa cagcatgatg tgaacgaact gaacgtgttt   1620
ttttatctgg atgcgcagaa agtgccggaa ggcgaaaaca acgtgaatct gaccagctca   1680
attgataccg cgctgctgga acagccgaaa atctatacct tttttagcag cgaattcatc   1740
aacaacgtga acaaaccggt gcaggcggcg ctgtttgtga gctggattca gcaggtgctg   1800
gttgatttta ccaccgaagc gaaccagaaa agcaccgtgg ataaaattgc ggatattagc   1860
attgtggtgc cgtatattgg cctggccctg aacattggca acgaagcgca gaaaggcaac   1920
tttaaagatg cgctggaact gctgggtgcg ggcattctgc tggaatttga accggaactg   1980
ctgattccga ccattctggt gtttaccatc aaaagctttc tgggcagcag cgataacaaa   2040
aacaaagtga tcaaagcgat taacaacgcg ctgaaagaac gtgatgaaaa atggaaagaa   2100
gtgtatagct tcattgtgtc taactggatg accaaaatca acacccagtt caacaaacgt   2160
aaagaacaaa tgtatcaggc gctgcagaac caggtgaacg cgattaaaac catcatcgaa   2220
agcaaataca acagctacac cctggaagaa aaaaacgaac tgaccaacaa atatgacatc   2280
aaacaaatcg aaaatgaact gaaccagaaa gtgagcattg ccatgaacaa cattgatcgc   2340
tttctgaccg aaagcagcat tagctacctg atgaaactga tcaacgaagt gaaaatcaac   2400
aaactgcgcg aatatgatga aaacgtgaaa acctacctgc tgaactatat tattcagcat   2460
ggcagcattc tgggcgaaag ccagcaagaa ctgaacagca tggttaccga taccctgaac   2520
aacagcattc cgtttaaact gagcagctac accgatgata aaatcctgat cagctacttc   2580
aacaaattct tcaaacgcat caaaagcagc agcgtgctga acatgcgtta taaaaacgat   2640
aaatacgtag ataccagcgg ctatgatagc aatatcaaca ttaacggtga tgtgtataaa   2700
tacccgacca acaaaaacca gttcggcatc tacaacgata aactgagcga agtgaacatt   2760
```

-continued

```
agccagaacg attatatcat ctacgataat aaatataaaa acttcagcat cagcttttgg   2820

gtgcgtattc cgaactacga taacaaaatc gtgaacgtga acaacgaata caccatcatt   2880

aactgcatgc gtgataacaa cagcggctgg aaagtgagcc tgaaccataa cgaaatcatc   2940

tggaccctgc aggataacgc cggcattaac cagaaactgg cctttaacta tggcaacgcg   3000

aacggcatta gcgattacat caacaaatgg atctttgtga ccattaccaa cgatcgtctg   3060

ggcgatagca aactgtatat taacggcaac ctgatcgacc agaaaagcat tctgaacctg   3120

ggcaacattc atgtgagcga taacatcctg ttcaaaattg tgaactgcag ctatacccgt   3180

tatattggca tccgctattt caacatcttc gataaagaac tggatgaaac cgaaattcag   3240

accctgtata gcaacgaacc gaacaccaac atcctgaaag atttctgggg caactatctg   3300

ctgtacgata aagaatatta tctgctgaac gtgctgaaac cgaacaactt tattgatcgc   3360

cgtaaagata gcaccctgag cattaacaac attcgtagca ccattctgct ggccaaccgt   3420

ctgtatagcg gcattaaagt gaaaattcag cgcgtgaaca atagcagcac caacgataac   3480

ctggtgcgta aaaacgatca ggtgtatatc aactttgtgg ccagcaaaac ccacctgttt   3540

ccgctgtatg cggataccgc gaccaccaac aaagaaaaaa ccattaaaat cagcagcagc   3600

ggcaaccgtt ttaaccaggt ggtggtgatg aacagcgtgg gcaacaactg tacaatgaac   3660

ttcaaaaaca acaacggcaa caacattggc ctgctgggct ttaaagcgga taccgtggtg   3720

gcgagcacct ggtattatac ccacatgcgt gatcatacca acagcaacgg ctgcttttgg   3780

aactttatta gcgaagaaca tggctggcag gaaaaatga                          3819
```

```
<210> SEQ ID NO 12
<211> LENGTH: 1272
<212> TYPE: PRT
<213> ORGANISM: artificial
<220> FEATURE:
<223> OTHER INFORMATION: recombinant protein BONT/E with MDM2 binding
      motif

<400> SEQUENCE: 12

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
```

-continued

```
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
    450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
    530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590
```

```
Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala  Asn Gly Ile Ser Asp  Tyr Ile Asn
        995                 1000                 1005
```

-continued

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 13
<211> LENGTH: 3819
<212> TYPE: DNA
<213> ORGANISM: Artificial
<220> FEATURE:
<223> OTHER INFORMATION: recombinant protein BONT/E with MDM2 binding motif

<400> SEQUENCE: 13
atgccgaaaa tcaacagctt caactataac gatccggtga acgatcgtac catcctgtat 60
attaaaccgg gcggttgcca ggaattttac aaaagcttca acatcatgaa aaacatctgg 120
attattccgg aacgtaacgt gattggcacc accccgcagg attttcatcc gccgaccagc 180
ctgaaaaacg gcgatagcag ctattatgat ccgaactatc tgcagtctga tgaagaaaaa 240
gatcgcttcc tgaaaatcgt gaccaaaatc ttcaaccgca tcaacaacaa cctgagcggc 300
ggcattctgc tggaagaact gagcaaagcg aatccgtatc tgggcaacga taacactcca 360
gataaccagt ttcatattgg tgatgcgagc gcggtggaaa ttaaatttag caacggctct 420

-continued

```
caggacattc tgctgccgaa cgtgattatt atgggcgcgg aaccggacct gtttgaaacc    480
aacagcagca acattagcct gcgtaacaac tatatgccga gcaaccatgg ttttggcagc    540
attgcgattg tgacctttag cccggaatat agctttcgct tcaacgataa cagcatgaac    600
gaatttattc aggacccggc gctgaccctg atgcacgagc tgattcatag cctgcatggc    660
ctgtatggcg cgaaaggcat taccaccaaa tataccatca cccagaaaca gaatccgctg    720
attaccaaca ttcgtggcac caacattgaa gaatttctga cctttggcgg caccgatctg    780
aacattatta ccagcgcgca gagcaacgat atctatacca acctgctggc cgattataaa    840
aaaatcgcgt ctaaactgag caaagtgcag gtgagcaatc cgctgctgaa tccgtataaa    900
gatgtgtttg aagcgaaata tggcctggat aaagatgcta gcggcattta tagcgtgaac    960
atcaacaaat tcaacgacat cttcaaaaaa ctgtatagct ttaccgaatt tgatctggcc   1020
accaaatttc aggtgaaatg ccgccagacc tatattggcc agtataaata ttttaaactg   1080
agcaacctgc tgaacgatag catttacaac atcagcgaag gctataacat caacaacctg   1140
aaagtgaact ttcgtggcca gaacgcgaat ttaaatccgc gtattattac cccgattacc   1200
ggccgtggac tagtgaaaaa aattatccgt ttttgcgtgc gtggcattat caccagcctg   1260
acctttgaac ataattgggc acagctggaa aacaaaagcc tggtgccgcg tggcagcaaa   1320
gcgttaaatg atttatgcat cgaaatcaac aacggcgaac tgttttttgt ggcgagcgaa   1380
aacagctata acgatgataa catcaacacc ccgaaagaaa ttgatgatac cgtgaccagc   1440
aataacaact acgaaaacga tctggatcag gtgattctga actttaacag cgaaagcgca   1500
ccgggcctgt ctgatgaaaa actgaacctg accattcaga acgatgcgta tatcccgaaa   1560
tatgatagca acggcaccag cgatattgaa cagcatgatg tgaacgaact gaacgtgttt   1620
ttttatctgg atgcgcagaa agtgccggaa ggcgaaaaca acgtgaatct gaccagctca   1680
attgataccg cgctgctgga acagccgaaa atctatacct tttttagcag cgaattcatc   1740
aacaacgtga acaaaccggt gcaggcggcg ctgtttgtga gctggattca gcaggtgctg   1800
gttgatttta ccaccgaagc gaaccagaaa agcaccgtgg ataaaattgc ggatattagc   1860
attgtggtgc cgtatattgg cctggccctg aacattggca acgaagcgca gaaaggcaac   1920
tttaaagatg cgctggaact gctgggtgcg ggcattctgc tggaatttga accggaactg   1980
ctgattccga ccattctggt gtttaccatc aaaagctttc tgggcagcag cgataacaaa   2040
aacaaagtga tcaaagcgat taacaacgcg ctgaaagaac gtgatgaaaa atggaaagaa   2100
gtgtatagct tcattgtgtc taactggatg accaaaatca acacccagtt caacaaacgt   2160
aaagaacaaa tgtatcaggc gctgcagaac caggtgaacg cgattaaaac catcatcgaa   2220
agcaaataca acagctacac cctggaagaa aaaaacgaac tgaccaacaa atatgacatc   2280
aaacaaatcg aaaatgaact gaaccagaaa gtgagcattg ccatgaacaa cattgatcgc   2340
tttctgaccg aaagcagcat tagctacctg atgaaactga tcaacgaagt gaaaatcaac   2400
aaactgcgcg aatatgatga aaacgtgaaa acctacctgc tgaactatat tattcagcat   2460
ggcagcattc tgggcgaaag ccagcaagaa ctgaacagca tggttaccga taccctgaac   2520
aacagcattc cgtttaaact gagcagctac accgatgata aaatcctgat cagctacttc   2580
aacaaattct tcaaacgcat caaaagcagc agcgtgctga acatgcgtta taaaaacgat   2640
aaatacgtag ataccagcgg ctatgatagc aatatcaaca ttaacggtga tgtgtataaa   2700
tacccgacca acaaaaacca gttcggcatc tacaacgata aactgagcga agtgaacatt   2760
agccagaacg attatatcat ctacgataat aaatataaaa acttcagcat cagcttttgg   2820
```

```
gtgcgtattc cgaactacga taacaaaatc gtgaacgtga acaacgaata caccatcatt   2880

aactgcatgc gtgataacaa cagcggctgg aaagtgagcc tgaaccataa cgaaatcatc   2940

tggaccctgc aggataacgc cggcattaac cagaaactgg cctttaacta tggcaacgcg   3000

aacggcatta gcgattacat caacaaatgg atctttgtga ccattaccaa cgatcgtctg   3060

ggcgatagca aactgtatat taacggcaac ctgatcgacc agaaaagcat tctgaacctg   3120

ggcaacattc atgtgagcga taacatcctg ttcaaaattg tgaactgcag ctatacccgt   3180

tatattggca tccgctattt caacatcttc gataaagaac tggatgaaac cgaaattcag   3240

accctgtata gcaacgaacc gaacaccaac atcctgaaag atttctgggg caactatctg   3300

ctgtacgata aagaatatta tctgctgaac gtgctgaaac cgaacaactt tattgatcgc   3360

cgtaaagata gcaccctgag cattaacaac attcgtagca ccattctgct ggccaaccgt   3420

ctgtatagcg gcattaaagt gaaaattcag cgcgtgaaca atagcagcac caacgataac   3480

ctggtgcgta aaaacgatca ggtgtatatc aactttgtgg ccagcaaaac ccacctgttt   3540

ccgctgtatg cggataccgc gaccaccaac aaagaaaaaa ccattaaaat cagcagcagc   3600

ggcaaccgtt ttaaccaggt ggtggtgatg aacagcgtgg gcaacaactg tacaatgaac   3660

ttcaaaaaca acaacggcaa caacattggc ctgctgggct ttaaagcgga taccgtggtg   3720

gcgagcacct ggtattatac ccacatgcgt gatcatacca acagcaacgg ctgcttttgg   3780

aactttatta gcgaagaaca tggctggcag gaaaaatga                          3819
```

```
<210> SEQ ID NO 14
<211> LENGTH: 1272
<212> TYPE: PRT
<213> ORGANISM: artificial
<220> FEATURE:
<223> OTHER INFORMATION: recombinant protein BONT/E with MDM2 binding
      motif

<400> SEQUENCE: 14

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175
```

-continued

```
Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Glu Asn Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
    450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
    530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
```

-continued

```
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala  Asn Gly Ile Ser Asp  Tyr Ile Asn
        995                 1000                1005

Lys Trp  Ile Phe Val Thr Ile  Thr Asn Asp Arg Leu  Gly Asp Ser
    1010                1015                1020
```

```
Lys Leu  Tyr Ile Asn Gly Asn  Leu Ile Asp Gln Lys  Ser Ile Leu
    1025                 1030                 1035

Asn Leu  Gly Asn Ile His Val  Ser Asp Asn Ile Leu  Phe Lys Ile
    1040                 1045                 1050

Val Asn  Cys Ser Tyr Thr Arg  Tyr Ile Gly Ile Arg  Tyr Phe Asn
    1055                 1060                 1065

Ile Phe  Asp Lys Glu Leu Asp  Glu Thr Glu Ile Gln  Thr Leu Tyr
    1070                 1075                 1080

Ser Asn  Glu Pro Asn Thr Asn  Ile Leu Lys Asp Phe  Trp Gly Asn
    1085                 1090                 1095

Tyr Leu  Leu Tyr Asp Lys Glu  Tyr Tyr Leu Leu Asn  Val Leu Lys
    1100                 1105                 1110

Pro Asn  Asn Phe Ile Asp Arg  Arg Lys Asp Ser Thr  Leu Ser Ile
    1115                 1120                 1125

Asn Asn  Ile Arg Ser Thr Ile  Leu Leu Ala Asn Arg  Leu Tyr Ser
    1130                 1135                 1140

Gly Ile  Lys Val Lys Ile Gln  Arg Val Asn Asn Ser  Ser Thr Asn
    1145                 1150                 1155

Asp Asn  Leu Val Arg Lys Asn  Asp Gln Val Tyr Ile  Asn Phe Val
    1160                 1165                 1170

Ala Ser  Lys Thr His Leu Phe  Pro Leu Tyr Ala Asp  Thr Ala Thr
    1175                 1180                 1185

Thr Asn  Lys Glu Lys Thr Ile  Lys Ile Ser Ser Ser  Gly Asn Arg
    1190                 1195                 1200

Phe Asn  Gln Val Val Val Met  Asn Ser Val Gly Asn  Asn Cys Thr
    1205                 1210                 1215

Met Asn  Phe Lys Asn Asn Asn  Gly Asn Asn Ile Gly  Leu Leu Gly
    1220                 1225                 1230

Phe Lys  Ala Asp Thr Val Val  Ala Ser Thr Trp Tyr  Tyr Thr His
    1235                 1240                 1245

Met Arg  Asp His Thr Asn Ser  Asn Gly Cys Phe Trp  Asn Phe Ile
    1250                 1255                 1260

Ser Glu  Glu His Gly Trp Gln  Glu Lys
    1265                 1270


<210> SEQ ID NO 15
<211> LENGTH: 12
<212> TYPE: PRT
<213> ORGANISM: Mus musculus

<400> SEQUENCE: 15

Thr Leu Ser Ser Gln His Asn Thr Tyr Thr Ile Glu
1               5                   10


<210> SEQ ID NO 16
<211> LENGTH: 7
<212> TYPE: PRT
<213> ORGANISM: Mus musculus

<400> SEQUENCE: 16

Lys Asp Gly Ser His Ser Thr
1               5


<210> SEQ ID NO 17
<211> LENGTH: 13
<212> TYPE: PRT
<213> ORGANISM: Mus musculus
```

<400> SEQUENCE: 17

Gly Val Gly Asp Thr Ile Lys Glu Gln Phe Val Tyr Val
1 5 10

<210> SEQ ID NO 18
<211> LENGTH: 10
<212> TYPE: PRT
<213> ORGANISM: Mus musculus

<400> SEQUENCE: 18

Gly Tyr Thr Phe Asn Thr Tyr Ala Val Asn
1 5 10

<210> SEQ ID NO 19
<211> LENGTH: 19
<212> TYPE: PRT
<213> ORGANISM: Mus musculus

<400> SEQUENCE: 19

Arg Ile Arg Ser Lys Ser Tyr Asn Tyr Val Thr Tyr Tyr Ala Asp Ser
1 5 10 15

Val Lys Asp

<210> SEQ ID NO 20
<211> LENGTH: 10
<212> TYPE: PRT
<213> ORGANISM: Mus musculus

<400> SEQUENCE: 20

Gly Asn Gly Asn Tyr Val Ser Phe Ala Tyr
1 5 10

<210> SEQ ID NO 21
<211> LENGTH: 115
<212> TYPE: PRT
<213> ORGANISM: Mus musculus

<400> SEQUENCE: 21

Gln Leu Val Leu Thr Gln Ser Ser Ser Ala Ser Phe Ser Leu Gly Ala
1 5 10 15

Ser Ala Lys Leu Thr Cys Thr Leu Ser Ser Gln His Asn Thr Tyr Thr
20 25 30

Ile Glu Trp Tyr Gln Gln Gln Pro Leu Lys Pro Pro Lys Tyr Val Met
35 40 45

Glu Leu Lys Lys Asp Gly Ser His Ser Thr Gly Asp Gly Ile Pro Asp
50 55 60

Arg Phe Ser Gly Ser Ser Ser Gly Ala Asp Arg Tyr Leu Ser Ile Ser
65 70 75 80

Asn Ile Gln Pro Glu Asp Glu Ala Ile Tyr Ile Cys Gly Val Gly Asp
85 90 95

Thr Ile Lys Glu Gln Phe Val Tyr Val Phe Gly Gly Gly Thr Lys Val
100 105 110

Thr Val Leu
115

<210> SEQ ID NO 22
<211> LENGTH: 121
<212> TYPE: PRT
<213> ORGANISM: Mus musculus -continued

```
<400> SEQUENCE: 22

Glu Val Gln Leu Val Glu Ser Gly Gly Gly Leu Val Gln Pro Lys Gly
1               5                   10                  15

Ser Leu Lys Leu Ser Cys Ala Ala Ser Gly Tyr Thr Phe Asn Thr Tyr
            20                  25                  30

Ala Val Asn Trp Val Arg Gln Ala Pro Gly Lys Gly Leu Glu Trp Val
        35                  40                  45

Ala Arg Ile Arg Ser Lys Ser Tyr Asn Tyr Val Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Lys Gly Asn Gly Asn Tyr Val Ser Phe Ala Tyr Trp Gly
            100                 105                 110

Gln Gly Thr Leu Val Thr Val Ser Ala
        115                 120
```

MEANS AND METHODS FOR THE DETERMINATION OF THE BIOLOGICAL ACTIVITY OF BONT/E IN CELLS

The present invention pertains to a polyclonal or monoclonal antibody specifically binding to BoNT/E-cleaved SNAP-25. Further, the invention provides a method for directly determining the biological activity of BoNT/E in cells, comprising the steps of: a) incubating cells susceptible to BoNT/E intoxication with BoNT/E for a time and under conditions which allow for the BoNT/E to exert its biological activity; b) fixing the cells and, optionally, permeabilizing the cells with a detergent; c) contacting the cells with at least a first capture antibody specifically binding to non-cleaved and BoNT/E-cleaved SNAP-25, and with at least a second capture antibody specifically binding to BoNT/E-cleaved SNAP-25, wherein the second capture antibody is an antibody of the invention, under conditions which allow for binding of said capture antibodies to the indicated substrates; d) contacting the cells with at least a first detection antibody specifically binding to the first capture antibody, under conditions which allow for binding of said first detection antibody to said first capture antibody, thus forming first detection complexes, and with at least a second detection antibody specifically binding to the second capture antibody, under conditions which allow for binding of said second detection antibody to said second capture antibody, thus forming second detection complexes, and wherein the first detection antibody is different from the second detection antibody; e) determining the amount of the first and second detection complexes of step d); and f) calculating the amount of SNAP-25 cleaved by BoNT/E in said cells by means of the second detection complexes, thereby determining the biological activity of BoNT/E in said cells. Furthermore, the invention relates to a kit for carrying out the method of the invention.

*Clostridium botulinum* and *Clostridium tetani* produce highly potent Neurotoxins, i.e. Botulinum toxins (BoNTs) and Tetanus toxin (TeNT), respectively. These Clostridial Neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s).

Alternatively, Clostridial Neurotoxins can be produced in heterologous cells, i.e. be produced recombinantly by expressing nucleic acid sequences encoding a Neurotoxin in appropriate host cells. Methods for the recombinant expression of Clostridial Neurotoxins in *E. coli* are well known in the art; see, for example, WO 00/12728, WO 01/14570, WO 2006/076902 or WO 2013/091895. In certain cases, the light and heavy chains are separately obtained, and then reconstituted in vitro; see WO 95/32738.

Furthermore, Clostridial Neurotoxins have been expressed in eukaryotic expression systems, such as in *Pichia pastoris, Pichia methanolica, S. cerevisiae*, insect cells and mammalian cells; see WO 2006/017749.

In all these expression systems, a proteolytic cleavage of the single chain Neurotoxin precursor is required, either by host cell enzymes during fermentation, or by adding proteolytic enzymes to the raw protein material isolated after fermentation, in order to generate the final biologically active Clostridial Neurotoxin protein comprising a light chain and a heavy chain, linked by a disulfide bond.

Active Neurotoxin consists of two chains, an N-terminal light chain of approx. 50 kDa and a C-terminal heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum Neurotoxins are synthesized as molecular complexes comprising the 150 kDa Neurotoxin protein and associated non-toxic proteins. The complex sizes differ based on the Clostridial strain and the distinct Neurotoxin serotypes ranging from 300 kDa, over 500 kDa, and 900 kDa. The non-toxic proteins in these complexes stabilize the Neurotoxin and protect it against degradation; see Silberstein 2004, Pain Practice 4, S19-526.

*Clostridium botulinum* secretes seven antigenically distinct serotypes designated A to G of the Botulinum Neurotoxin (BoNT). All serotypes together, with the related Tetanus Neurotoxin (TeNT) secreted by *Clostridium tetani*, are $Zn^{2+}$-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447.

Despite its toxic effects, Botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharmaceuticals, GmbH). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic effect.

The Clostridial Neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial Neurotoxins, the qualitative and quantitative determination of said Neurotoxins as well as the quality control of the biologically active Neurotoxin polypeptides is of particular importance. In addition, governmental agencies accept only simple, reliable, and validated Botulinum toxin activity assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with this type of animal-based assays. In addition, the regulatory agencies are engaging pharmaceutical companies to apply the "three Rs" principle to the potency testing of Botulinum Neurotoxins: "Reduce, Refine, Replace"; see Straughan, Altern. Lab. Anim. (2006), 34, 305-313. As a consequence, cell-based test systems have been developed in order to provide reasonable alternatives to methods using live animals. Yet, only a few cellular test systems are available for the determination of Neurotoxin biological activity thus far which have been shown to be sufficiently sensitive to Neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a subclone of the SiMa cell line (WO 2010/105234 A1).

However, the isolation of primary neurons requires the killing of animals and is laborious and time consuming. Further, test systems using different primary neurons show large variances. Similarly, the generation of neuronal differentiated induced pluripotent stem cells is difficult and time consuming. In addition, storage of such cells is very problematic. Assays using tumor cell lines are frequently not sensitive enough to BoNT. Moreover, complex differentiation protocols are required for said tumor cell lines which result in large variances and/or high failure rates of assays using said cell lines.

Assays for determining the biological activity of Clostridial Neurotoxins described in the art include Western blot analysis in which the Neurotoxin activity is quantified by the amount of cleaved Neurotoxin substrate in cell lysates. In other assays, the activity of Clostridial Neurotoxins is measured by an electrochemoluminescence (ECL) sandwich ELISA; see WO 2009/114748 A1. Also in this case, the biological activity of the Clostridial Neurotoxin is determined by the detection of cleaved Clostridial Neurotoxin substrate after isolation from the cell lysate. Further, the Neurotoxin substrate has to be concentrated, in both assays.

In light of the above, further test systems for the determination of Neurotoxin polypeptide activity acceptable to governmental agencies and/or providing for an alternative to animal-based test systems are highly desirable.

Thus, the technical problem underlying the present invention may be seen as the provision of means and methods complying with the aforementioned needs. The technical problem is solved by the embodiments characterized in the claims and herein below.

The present invention relates, in a first aspect, to a polyclonal or monoclonal antibody specifically binding to BoNT/E-cleaved SNAP-25. Further, the invention pertains to a deposited hybridoma cell line generating a monoclonal antibody specifically binding to BoNT/E-cleaved SNAP-25.

The present invention provides a novel antibody specifically binding to the cleavage site of the BoNT/E-cleaved SNAP-25, i.e. to BoNT/E-cleaved SNAP-25. In addition, the invention provides the hybridoma cell line pCNEI 32-7-1, 3614-000, producing the monoclonal antibody of the invention specifically binding to BoNT/E-cleaved SNAP-25. This hybridoma cell line has been deposited by the Applicant under the Budapest Treaty on Dec. 17, 2014, at DSMZ—Deutsche Sammlung von Mikroorganismen und Zellkulturen GmbH, Inhoffenstraße 7 B, 38124 Braunschweig, Germany under the accession number DSM ACC3261. As known in the art, SNAP-25 is a substrate of, inter alia, the BoNT/E neurotoxin. SNAP-25 has a total length of 206 amino acid residues. The BoNT/E cleavage site in SNAP-25 is positioned between Arginine (R) 180 and Isoleucine (I) 181, also referred to as "$R_{180}I$". Accordingly, the cleavage of SNAP-$25_{206}$ by BoNT/E reveals two fragments, i.e. an N-terminal fragment from amino acid residues 1 to 180, in the following also referred to as "SNAP-$25_{180}$ cleavage product" and a C-terminal fragment from amino acid residues 181 to 206. The antibody of the invention has been generated and characterized as described in the following Examples. Briefly, a mouse monoclonal antibody has been produced by immunizing mice with the peptide "C-NEIDTQNRQIDR-OH" (SEQ ID NO: 1) coupled to an immunization protein. The shown data indicate that this antibody detects specifically the SNAP-$25_{180}$ cleavage product. Thus, this antibody is particularly suitable for assays for measuring the biological activity of BoNT/E by the detection of BoNT/E-cleaved SNAP-25. Specifically, it can be used as second capture antibody for the method of the invention which allows for determining the biological activity of BoNT/E directly in cells, due to its high affinity and specificity for the SNAP-$25_{180}$ cleavage product, relative to the SNAP-$25_{206}$ uncleaved substrate. Such an antibody is not yet commercially available. Further envisaged by the present invention is a polyclonal antiserum or antibody which can be generated, e.g., by coupling the peptide "C-NEIDTQNRQIDR-OH" (SEQ ID NO: 1) to an immunization protein and immunizing species including but not limited to, e.g., rabbit, goat, horse, donkey, mouse, rat, or llama.

As used herein, the term "antibody" refers to a molecule generated by an immune system that was made in response to a particular antigen that specifically binds to that antigen, and includes both naturally occurring antibodies and non-naturally occurring antibodies. An "antibody" as used herein encompasses a monoclonal antibody, a polyclonal antiserum or antibody, a single chain antibody, a dimer or a multimer, a chimerized antibody, a bispecific antibody, a bispecific single chain antibody, a multispecific antibody, a synthetic antibody, a humanized antibody, a bifunctional antibody, a cell-associated antibody like an Ig receptor, a linear antibody, a diabody, a minibody, or a fragment of any of said antibodies. Fragments of said antibodies include, e.g., Fab, Fv, or scFv fragments, or chemically modified derivatives of any of these fragments. Antibodies can be manufactured by using methods which are described in the art; see, for example, Harlow and Lane "Antibodies, A Laboratory Manual", CSH Press, Cold Spring Harbor, 1988. Monoclonal antibodies can be prepared by the techniques originally described in Kohler 1975, Nature 256, 495, and Galfré 1981, Meth. Enzymol. 73, 3. Said techniques comprise the fusion of mouse myeloma cells to spleen cells derived from immunized mammals. Antibodies can be further improved by techniques well known in the art. For example, surface plasmon resonance as employed in the Biacore system can be used to increase the efficiency of phage antibodies which bind to the epitope; see, e.g., Schier 1996, Human Antibodies Hybridomas 7, 97; Malmborg 1995, J. Immunol. Methods 183, 7. Antibodies as used herein also comprise functional equivalents of antibodies, i.e. agents which are capable of specifically binding to the desired epitope(s) or parts of the BoNT/E-cleaved SNAP-25 substrate. In an aspect, such functional equivalents comprise binding proteins specifically binding to the BoNT/E-cleaved SNAP-25 or domains thereof which are capable of mediating the said specific binding. An antibody as used herein can be a full-length immunoglobulin molecule comprising the VH and VL domains, as well as a light chain constant domain (CL) and heavy chain constant domains, CH, CH2 and CH3, or an immunologically active fragment of a full-length immunoglobulin molecule, such as, e.g., a Fab fragment, a $F(ab')_2$ fragment, a Fc fragment, a Fd fragment, or a Fv fragment. An antibody can be derived from any vertebrate species (e.g., human, monkey, goat, horse, donkey, mouse, rat, rabbit, or chicken), and can be of any type (e.g., IgG, IgE, IgM, IgD, or IgA), class (e.g., IgA, IgD, IgE, IgG, or IgM) or subclass (IgG1, IgG2, IgG3, IgG4, IgA1 or IgA2). For general disclosure on the structure of naturally occurring antibodies, non-naturally occurring antibodies, and antigenic compound-binding fragments thereof, it is referred to, e.g., Plueckthun in The Pharmacology of Monoclonal Antibodies, vol. 113, Rosenburg and Moore eds., Springer-Verlag, New York, pp. 269-315 (1994); Borrabeck, Antibody Engineering 2nd ed. (Oxford University Press). Naturally occurring antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody, i.e., the Fv fragment. This fragment includes a dimer of one heavy chain variable domain (VH) and one light chain variable domain (VL) in tight, non-covalent association. Each domain comprises four framework regions (FR), which largely adopt a beta-sheet configuration, connected by three hypervariable regions, which form loops connecting, and in some cases form part of, the beta-sheet structure. Each hypervariable region comprises an amino acid sequence corresponding to a complementarity determining region (CDR). Collectively, it is the three-dimensional configuration of the six CDR regions (three CDR regions on the light chain, i.e. CDR-L1, CDR-L2 and CDR-L3 and three CDR regions on the heavy chain, i.e. CDR-H1, CDR-H2 and CDR-H3) that defines an antigen-binding site on the surface of the VH-VL dimer that confers antigen-binding specificity. See e.g., Cyrus Chothia, et al., Conformations of Immunoglobulin Hypervariable Regions, Nature 342(6252): 877-883 (1989); Elvin A. Kabat, et al. Sequences of Proteins of Immunological Interest, 5th Ed. Public Health Service, National Institutes of Health, Bethesda, Md. (1991). The constant domains of the antibody are not involved directly in binding an antibody to an antigen, but exhibit various effector functions, such as participation of the antibody in antibody dependent cellular cytotoxicity.

“Selective binding” or “specific binding” as used herein means that the antibody of the present invention specifically binds to BoNT/E-cleaved SNAP-25 but does not cross-react to a significant extent with non-cleaved SNAP-25, or with other polypeptides in general. Epitope specificity is an important characteristic of the antibody of the present invention. The antibody of the invention specifically binds to an epitope consisting of a peptide having an amino acid sequence as shown in SEQ ID NO: 1, 2, 3, 4, 5, 6, 7 or 8. Specific binding can be tested by various well known techniques including, e.g., competition studies. Another important characteristic is the sensitivity of the antibody. Sensitivity shall be, in one aspect of the invention, such that at least 70%, at least 80%, at least 90%, at least 95% of the BoNT/E-cleaved SNAP-25 comprised by a sample or cell is bound. Sensitivity can be tested by well known techniques. Those skilled in the art will be able to determine operative and optimal assay conditions for each determination by employing routine experimentation. Conventional techniques for binding studies include radioimmunoassay, ELISA, equilibrium dialysis, isothermal microcalorimetry, BIACORE® assays (surface plasmon reasonance, SPR) or other surface adsorption methods. The BIACORE® SPR system measures the antibody-antigen interaction. SPR response reflects a change in mass concentration at the detector surface as analytes bind or dissociate. Based on SPR, real-time BIACORE® measurements monitor interactions directly as they occur, see BIAapplications Handbook, version AB (reprinted 1998), BIACORE® code No: BR-1001-86; BIAtechnology Handbook, version AB (reprinted 1998), BIACORE® code No: BR-1001-84. The binding properties such as sensitivity of an antibody of the present invention may, in principle, be determined by binding studies using an immobilized antigen such as a peptide having an amino acid sequence as shown in SEQ ID NO: 2 (“NEIDTQNRQIDR”) (the ligand) presented on a sensor surface. The antibody to be tested (the analyte) will be provided in the mobile phase, i.e. in a solution. In some cases, the antigen is attached indirectly to the surface through binding to another immobilized molecule which is referred as the “capturing molecule”. When the antibody is injected in a discrete pulse across the surface with the immobilized antigens, essentially three phases can be subdivided: (i) association of antibody with the antigen during sample injection; (ii) equilibrium or steady state during sample injection, where the rate of antibody binding is balanced by dissociation from the antibody-antigen complex; (iii) dissociation of the antibody from the surface during buffer flow. It will be understood that such an assay can alternatively be performed with immobilized antibodies to be investigated and an antigen containing solution as the mobile phase. The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$). Accordingly, “selective binding” or “specific binding” as used herein includes binding properties such as, e.g., binding affinity, binding specificity, and binding avidity; see, e.g., David J. King, Applications and Engineering of Monoclonal Antibodies, pp. 240 (1998). Binding affinity refers to the length of time the antibody resides at its epitope binding site, and can be viewed as the strength with which an antibody binds its epitope. Binding affinity can be described an antibody’s equilibrium dissociation constant (KD), which is defined as the ratio Kd/Ka at equilibrium. Ka is the antibody’s association rate constant and Kd is the antibody’s dissociation rate constant. Binding affinity is determined by both the association and the dissociation and alone neither high association nor low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in $M^{-1} s^{-1}$, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in $s^{-1}$, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]×[Ag]/[Ab+Ag], where [Ab] is the molar concentration of the antibody, [Ag] is the molar concentration of the antigen, and [Ab+Ag] is the of molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen.

A target antigen such as the BoNT/E substrate SNAP-25 generally has one or more binding sites, also called epitopes, which are recognized by the CDR-formed antigen-binding site of the antibody. As used herein, an "epitope" is synonymous with "antigenic determinant" and refers to the site on a target antigen, such as, e.g., a peptide, polypeptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may have more than one corresponding antibody. "Specific binding" as referred to herein can be tested by various well known techniques including, e.g., competition experiments and Western blots. An epitope as used in accordance with the invention relates to the antigenic determinant in the BoNT/E-cleaved SNAP-25, which can be localized near, adjacent to or in the BoNT/E cleavage site of SNAP-25 which is recognized by the antibody. As used herein, the term "specifically" means selectively and refers to having a unique effect or influence or reacting in only one way or with only one thing. As used herein, the term "specifically binds" or "selectively binds" when made in reference to an antibody or binding protein or binding domain, refers to the discriminatory binding of the antibody or binding protein/domain to the indicated target epitope such that the antibody or binding protein/domain does not substantially cross-react with non-target epitopes. The minimal size of a peptide epitope, as defined herein, is about five amino acid residues, and a peptide epitope typically comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 30 amino acid residues. A peptide epitope may be a linear or a discontinuous epitope. A discontinuous epitope comprises amino acid residues that are not adjacent in the primary structure of the peptide but are brought together into an epitope by way of the secondary, tertiary or quaternary structure of the peptide. Furthermore, it is also noted that an epitope may comprise a portion of a molecule other than an amino acid sequence such as, e.g., carbohydrate moiety, lipid moiety like glycolipids or lipoproteins, or a chemically modified amino acid moiety like a phosphorylated amino acid.

In another aspect of the polyclonal or monoclonal antibody of the invention, the antibody specifically binds to an epitope consisting of a peptide having the amino acid sequence shown in SEQ ID NO: 1 ("C-NEIDTQNRQIDR-OH"). Preferably, the antibody of the invention recognizes and specifically binds to the epitope SNAP-$25_{169-180}$ "NEIDTQNRQIDR" shown in SEQ ID NO: 2 and/or to SNAP-$25_{180}$, i.e. BoNT/E-cleaved SNAP-25. More preferably, the antibodies of the invention recognize and specifically bind to the epitope SNAP-$25_{170-180}$ "EIDTQNRQIDR" shown in SEQ ID NO: 3 and/or to SNAP-$25_{180}$, to the epitope SNAP-$25_{171-180}$ "IDTQNRQIDR" of the sequence shown in SEQ ID NO: 4 and/or to SNAP-$25_{180}$, to the epitope SNAP-$25_{172-180}$ "DTQNRQIDR" shown in SEQ ID NO: 5 and/or to SNAP-$25_{180}$, to the epitope SNAP-$25_{173-180}$ "TQNRQIDR" shown in SEQ ID NO: 6 and/or to SNAP-$25_{180}$, to the epitope SNAP-$25_{174-180}$ "QNRQIDR" shown in SEQ ID NO: 7 and/or to SNAP-$25_{180}$, or to the epitope SNAP-$25_{175-180}$ "NRQIDR" shown in SEQ ID NO: 8 and/or to SNAP-$25_{180}$.

In one aspect of the monoclonal antibody of the invention, the monoclonal antibody is produced by the hybridoma cell line pCNEI 32-7-1, 3614-000 which has been deposited by the Applicant under the Budapest Treaty on Dec. 17, 2014, at DSMZ—Deutsche Sammlung von Mikroorganismen und Zellkulturen GmbH, Inhoffenstraße 7 B, 38124 Braunschweig, Germany under the accession number DSM ACC3261.

In a further aspect of the polyclonal or monoclonal antibody of the invention, the antibody has an equilibrium dissociation constant for BoNT/E-cleaved SNAP-25 of less than 100 nM, less than 50 nM less than 10 nM, less than 5 nM, less than 2 nM, less than 1 nM or preferably less than 0.5 nM.

In a still further aspect of the polyclonal or monoclonal antibody of the invention, the equilibrium dissociation constant of the antibody for BoNT/E-cleaved SNAP-25 is at least 10-fold, at least 50-fold or preferably at least 100-fold higher than for SNAP-25 not cleaved by BoNT/E, i.e. non-cleaved SNAP-25.

In another aspect of the polyclonal or monoclonal antibody of the invention, the antibody comprises at least one of the complementarity determining regions (CDRs) selected from CDR-L1 (SEQ ID NO. 15), CDR-L2 (SEQ ID NO. 16), CDR-L3 (SEQ ID NO. 17), CDR-H1 (SEQ ID NO. 18), CDR-H2 (SEQ ID NO. 19) and CDR-H3 (SEQ ID NO. 20) comprised by the monoclonal antibody produced by the hybridoma cell line pCNEI 32-7-1, 3614-000 deposited under the accession number DSM ACC3261. Preferably, the antibody comprises two, three, four, five or all six of the indicated CDRs.

In still another aspect of the polyclonal or monoclonal antibody of the invention, the antibody comprises the VH domain or VH region (SEQ ID NO. 22) and/or the VL domain or VL region (SEQ ID NO. 21) comprised by the monoclonal antibody produced by the hybridoma cell line pCNEI 32-7-1, 3614-000 deposited under the accession number DSM ACC3261.

In these aspects, the present invention relates to an antibody or a fragment thereof, which specifically binds to the cleavage site of the BoNT/E-cleaved SNAP-25 and which comprises a heavy chain variable region (VH) comprising an amino acid sequence shown in SEQ ID NO. 22 and/or a light chain variable region (VL) comprising an amino acid sequence shown in SEQ ID NO. 21, comprised by the monoclonal antibody produced by the hybridoma cell line pCNEI 32-7-1, 3614-000 deposited under the accession number DSM ACC3261. Further encompassed by the invention are antibodies or fragments thereof which comprise one, two or three complementarity determining regions (CDRs)

of said heavy chain and/or light chain variable region(s) or domain(s). The corresponding sequences of the CDR-H1 (SEQ ID NO. 18), CDR-H2 (SEQ ID NO. 19) and CDR-H3 (SEQ ID NO. 20) and the corresponding sequences of the CDR-L1 (SEQ ID NO. 15), CDR-L2 (SEQ ID NO. 16) and CDR-L3 (SEQ ID NO. 17), respectively, are comprised by the monoclonal antibody produced by the hybridoma cell line pCNEI 32-7-1, 3614-000 deposited under the accession number DSM ACC3261.

Preferably, the antibody of the invention is a monoclonal antibody. More preferably, the monoclonal antibody is the mouse monoclonal antibody generated and characterized in the following Examples, i.e. the monoclonal antibody produced by the hybridoma cell line pCNEI 32-7-1, 3614-000 deposited under the accession number DSM ACC3261. The above mentioned CDR, VH and VL sequences are the corresponding sequences of said antibody.

In a further aspect, the invention provides for a method for directly determining the biological activity of BoNT/E in cells, comprising the steps of:

a) incubating cells susceptible to BoNT/E intoxication with BoNT/E for a time and under conditions which allow for the BoNT/E to exert its biological activity;
b) fixing the cells and, optionally, permeabilizing the cells with a detergent;
c) contacting the cells with at least a first capture antibody specifically binding to non-cleaved and BoNT/E-cleaved SNAP-25, and with at least a second capture antibody specifically binding to BoNT/E-cleaved SNAP-25, under conditions which allow for binding of the first capture antibody to non-cleaved and BoNT/E-cleaved SNAP-25 and for binding of the second capture antibody to BoNT/E-cleaved SNAP-25;
d) contacting the cells with at least a first detection antibody specifically binding to the first capture antibody, under conditions which allow for binding of said first detection antibody to said first capture antibody, thus forming first detection complexes and with at least a second detection antibody specifically binding to the second capture antibody, under conditions which allow for binding of said second detection antibody to said second capture antibody, thus forming second detection complexes, and wherein the first detection antibody is different from the second detection antibody;
e) determining the amount of the first and second detection complexes of step d); and
f) calculating the amount of SNAP-25 cleaved by BoNT/E in said cells by means of the second detection complexes, thereby determining the biological activity of said BoNT/E in said cells.

In one aspect of the method of the invention, the second capture antibody used in step c) is the polyclonal or monoclonal antibody of the invention. In another aspect of the method of the invention, the second capture antibody used in step c) is a BoNT/E cleavage site-specific antibody as described in Jones et al., Journal of Immunological Methods 329 (2008), p. 92-101.

In the method of the invention, the BoNT/E-cleaved SNAP-25 can be directly detected in the cell(s). To this end, cells which are susceptible to BoNT/E intoxication as defined in more detail elsewhere herein are incubated with a BoNT/E Neurotoxin polypeptide for a time and under conditions which allow for the BoNT/E Neurotoxin polypeptide to exert its biological activity. In a next step, the cells are fixed and, depending on the used fixation agent, permeabilized, for example, by addition of a fixation agent such as methanol, ethanol, acetone, formaldehyde or mixtures of the mentioned fixation agents. Optionally, the cells can be additionally permeabilized by using at least one detergent as defined elsewhere herein such as Triton X-100, Tween 20, Saponin, Digitonin or n-Octyl-β-glucopyranoside. The detergent can be comprised in an appropriate buffer such as PBS. Thereafter, the cells are contacted with at least a first capture antibody which specifically binds to the BoNT/E non-cleaved and BoNT/E-cleaved SNAP-25 and with at least a second capture antibody specifically binding to BoNT/E-cleaved SNAP-25, e.g. an antibody specifically binding to the cleavage site of the BoNT/E-cleaved SNAP-25, under conditions which allow for binding of said first capture antibody to the non-cleaved and BoNT/E-cleaved SNAP-25 and the second capture antibody to BoNT/E-cleaved SNAP-25. Suitable epitopes, BoNT/E cleavage sites in SNAP-25 and methods for the generation of antibodies specifically binding to BoNT/E-cleaved SNAP-25 are described elsewhere herein. In addition, the present inventors have generated and characterized a monoclonal antibody which specifically binds to BoNT/E-cleaved SNAP-25, in the following Examples. Said antibody has high binding specificity for the SNAP-$25_{180}$ cleavage product that allows for the preferential recognition of this cleavage product relative to the SNAP-$25_{206}$ uncleaved substrate. The first capture antibody is able to determine the total content or amount of the BoNT/E substrate SNAP-25 in the cells, by binding specifically to an appropriate epitope present in both the BoNT/E non-cleaved and BoNT/E-cleaved SNAP-25. The second capture antibody recognizes and binds specifically to an epitope present only in the BoNT/E-cleaved SNAP-25 but not in the non-cleaved SNAP-25. Alternatively, the cells can be contacted with a mixture of said first and second capture antibodies, i.e. the cells are contacted with at least a first capture antibody and at least a second capture antibody simultaneously, under the mentioned conditions. In the next step, the cells are contacted with at least a first detection antibody specifically binding to the first capture antibody under conditions which allow for binding of said first detection antibody to said first capture antibody, thus forming first detection complexes. In a subsequent step, the cells are contacted with at least a second detection antibody specifically binding to the second capture antibody, under conditions which allow for binding of said second detection antibody to said second capture antibody, thus forming second detection complexes. Alternatively, the cells can be contacted with a mixture of said first and second detection antibodies, i.e. the cells are contacted with at least a first detection antibody and at least a second detection antibody simultaneously, under the mentioned conditions. Alternatively, permeabilized cells can be contacted with a mixture of said first and second capture antibodies and said first and second detection antibodies simultaneously, under the mentioned conditions. In the next step, the amounts of the first and second detection complexes are determined. Finally, the amount of SNAP-25 cleaved by BoNT/E in said cells is calculated by means of the second detection complexes. The term "calculating" as used in accordance with the method of the present invention relates to mathematical operations which allow for determining the amount of BoNT/E-cleaved SNAP-25 in the cell. Thereby, the biological activity of BoNT/E is determined directly in the cells. This means that no lysis of the cells and no isolation or concentration of the BoNT/E-cleaved SNAP-25 from cell lysates is necessary any longer, as in the methods described in the art. Further, the method of the invention is less time consuming, less laborious and more precise than, e.g., FRET-based assays used in the art.

The method of the invention is described in more detail, in the following. For cell culture, the cells susceptible to BoNT/E Neurotoxin polypeptide intoxication as defined herein, such as neuronal cells, SiMa cells or induced pluripotent stem cell (iPS)-derived neurons, are first seeded on 96 well microtiter plates. SiMa cells are differentiated to a neuronal phenotype, for example, according to the procedures disclosed in WO 2010/105234, and iPS-derived neurons are differentiated to a neuronal phenotype, e.g., according to assays described in WO 2012/135621. If necessary, the sensitivity, respectively homogeneity of the sensitivity of the cells susceptible to BoNT/E neurotoxin polypeptide could be optimized by using particular cell cultivation methods as disclosed in WO 2015/124618. Then, the cells are intoxicated with a BoNT/E Neurotoxin polypeptide for about 72 hours. In the subsequent step, the cells are fixed on the microtiter plate, prior to the ELISA assay. For fixing the cells, for example ice-cold methanol (−20° C.) can be added to the cells for 20 minutes at −20° C.

For performing the ELISA assay, the cells are first washed. As a wash buffer, e.g., 10 mM PBS buffer (pH 7.4) can be used. Thereafter, endogenous proteases are quenched by a quenching buffer such as 0.6% $H_2O_2$ in 10 mM PBS (pH 7.4), followed by another wash step. In the following step, free binding sites on the microtiter plate are blocked by an appropriate blocking buffer such as, for instance, 2% BSA in 10 mM PBS buffer (pH 7.4). Thereafter, the cells are washed by washing buffer as mentioned above.

In the next step, the fixed and permeabilized cells are incubated, e.g., with a mixture of two different antibodies. The mixture comprises a first capture antibody specifically binding to the BoNT/E non-cleaved and BoNT/E-cleaved substrate SNAP-25 and a second capture antibody specifically binding to the BoNT/E-cleaved SNAP-25, e.g. an antibody specifically binding to the BoNT/E cleavage site in the BoNT/E-cleaved SNAP-25. For this purpose, the polyclonal or monoclonal antibody of the invention is particularly suitable. Said first and second capture antibodies can also be applied subsequently. For example, the first capture antibody can specifically bind to both non-cleaved and BoNT/E-cleaved SNAP-25, thereby allowing for the quantification of the total amount or content of SNAP-25, i.e. BoNT/E-non-cleaved and BoNT/E-cleaved SNAP-25, in the cells. Further, this first capture antibody can be used for the normalization of the amount of BoNT/E-cleaved SNAP-25 in the cells, upon evaluation as described herein. The second capture antibody specifically binds to BoNT/E-cleaved SNAP-25 and therefore allows for the determination and detection of the BoNT/E-cleaved SNAP-25.

The following detection of the total (BoNT/E-non-cleaved and BoNT/E-cleaved) SNAP-25 and the BoNT/E-cleaved SNAP-25 in the method of the invention can be carried out directly on the microtiter plate or cell culture dish, i.e. within the cells. Advantageously, it is therefore not necessary to prepare cell extracts and to isolate and/or concentrate the BoNT/E-cleaved SNAP-25 from the cell lysate in the method of the invention, as in the methods described in the art. Thereafter, the cells are washed in order to remove excess antibody not bound to the respective antigen. In the subsequent step, the permeabilized cells are contacted with at least a first detection antibody and at least a second detection antibody. Said antibodies can be applied as a mixture, i.e. simultaneously, or subsequently. The first detection antibody specifically binds to the first capture antibody. Thereby, first detection complexes are being formed. The first detection antibody can be directed against the species from which the first capture antibody is derived from. For example, in case the rabbit polyclonal anti-SNAP-25 antibody S9684 (Sigma) is used as a first capture antibody specifically binding to the BoNT/E-non-cleaved and BoNT/E-cleaved substrate SNAP-25, an anti-rabbit alkaline phosphatase-conjugated antibody can be used as a first detection antibody. The second detection antibody specifically binds to the second capture antibody. Thereby, second detection complexes are being formed. The second detection antibody can be directed against the species from which the second capture antibody is derived from. For instance, in case the mouse monoclonal antibody (mAb) generated and characterized in the following Examples is used as a second capture antibody specifically binding to the BoNT/E-cleaved SNAP-25, an anti-mouse horseradish peroxidase (HRP)-conjugated antibody can be used as a second detection antibody. It is clear for those skilled in the art that the first detection antibody and the second detection antibody are conjugated with different enzymes in order to allow for the specific detection of the respective first and second capture antibody as used in the method of the invention. For instance, the HRP-based detection as described elsewhere herein can be used for the BoNT/E-cleaved SNAP-25 and the alkaline phosphatase-based detection for the total (BoNT/E-cleaved and BoNT-E-non-cleaved) SNAP-25. Thereafter, the cells are washed again. In a subsequent step, a fluorogenic HRP substrate is added to the cells. As a HRP substrate, e.g., Amplex UltraRed (Invitrogen) can be used which is excited at 540 nm and which emits at 600 nm. Incubation with the HRP substrate is carried out for a time sufficient for sufficient conversion of substrate by the horseradish peroxidase. Subsequent to the incubation with the HRP substrate, for example, the AP substrate DiFMUP (6,8-difluoro-4-methylumbelliferyl phosphate; excitation 360 nm; emission 450 nm) can be added to the HRP substrate and the cells are incubated with a mixture of said two substrates. Incubation with said AP substrate is carried out for a time which allows for sufficient conversion of substrate by the alkaline phosphatase. As known in the art, a substrate has to be converted in an amount which is sufficient so that the measured signal is at least as high as the mean value of the blank plus three standard deviations of the mean, according to the definition of limit of detection. The limit of detection can be determined as described in the literature; see, e.g., Armbruster and Pry, Clinical Biochem. Rev. 2008, 29 (Supplement 1): S49-S52. Because the pH optimum of the alkaline phosphatase is in the alkaline region, the corresponding substrate buffer is strongly alkaline. If the alkaline phosphatase substrate is added to the HRP substrate, the reaction of the horseradish peroxidase is stopped by the alkaline pH and the alkaline phosphatase converts DiFMUP. Converted HRP substrate is not influenced by the alkaline pH. Finally, the fluorescence of the two substrates is measured as follows:

Amplex UltraRed: Excitation 540 nm; emission 600 nm

DiFMUP: Excitation 360 nm; emission 450 nm

As appreciated by those skilled in the art, only those fluorogenic substrates are appropriate for detection of the first and second capture antibody in the method of the invention which exhibit different excitation/emission wave lengths of the used substrates. Only in this case, they allow for the specific detection of each antigen, i.e. the total SNAP-25 (BoNT/E non-cleaved and BoNT/E-cleaved SNAP-25) and the BoNT/E-cleaved SNAP-25. Thereby, it is possible to quantify the total content of SNAP-25 and the content of BoNT/E-cleaved SNAP-25 in every well or cell culture dish at the same time. In light of this, it is advantageously possible to automatize the method of the invention. As set forth elsewhere herein it is envisaged that the fluorogenic substrates chosen for the method of the invention exhibit a sufficient shift between the excitation/emission spectra in order to allow for the specific detection of the respective substrate. This requirement is fulfilled, for example, for the HRP substrate Amplex and its derivatives and for the AP substrate DiFMUP. Whereas, in an optimal case, there is no overlap between the excitation/emission spectra of the used fluorogenic substrates, it has been experienced that an overlap of up to 30% in the peak area of the excitation spectra of the used fluorogenic substrates is tolerable.

As further acknowledged by those skilled in the art, the method of the present invention allows for the direct detection and quantification of the substrate SNAP-25 cleaved by the Neurotoxin polypeptide BoNT/E in the cells, thereby determining the biological activity of said BoNT/E Neurotoxin polypeptide in said cells. Advantageously, the method of the invention does not require the preparation of cell lysates or extracts and the isolation or concentration of the BoNT/E-cleaved SNAP-25 from the cell lysates/extracts, which is necessary for the methods and assays known in the art. As a consequence of this, sample material can be saved. Further, the sample preparation and the number of samples can be reduced by the method of the invention since the amount of total SNAP-25 and the amount of BoNT/E-cleaved SNAP-25 in the sample can be determined at the same time. In the assays described in the art, the samples have to be subdivided in order to detect both antigens, i.e. total Neurotoxin substrate and cleaved Neurotoxin substrate, separately from each other. The method of the invention renders the subdivision of the sample unnecessary. Thereby, inhomogeneities resulting from the subdivision of samples can be avoided and sample material can be saved. Furthermore, antigens can be degraded in the assays described in the art which can falsify the detection of the cleaved Neurotoxin substrate. This is because in the assays described in the art, the cells are incubated with detergent-containing lysis buffers which, however, are not able to inactivate the Neurotoxin polypeptide or other endogenous proteases resulting in degradation of the Neurotoxin substrate upon longer storage of the samples. Stronger lysis buffers cannot be used in the ECL sandwich ELISA described in the prior art due to the required use of the cell lysate in said assay. This is because the aggregation of the above-mentioned antigens can result in unspecific adsorption of the antigens to the plastic surface of the cell culture dishes or microtiter plates which in turn disturbs the detection of the antigens by appropriate antibodies. Since the antibodies for the detection of the antigens get into contact with the lysate, too, the antibodies can also aggregate. In this case, no reliable and accurate detection of the antigen is possible anymore. The present inventors have experienced such degradation reactions by using Western blot assays for the detection of the biological activity of Neurotoxin activity described in the art. Upon longer storage of lysates at −20° C., in comparison to fresh lysate samples, the detection signal of total SNAP-25 has been found to be strongly reduced thereby reducing the sensitivity of the test system. It has been found by the present inventors that the degradation of SNAP-25 and/or the instability of the samples can be avoided by directly fixing the cells on the cell culture dish because both the BoNT/E Neurotoxin substrate SNAP-25 and the BoNT/E Neurotoxin or other endogenous proteases are inactivated immediately by aggregation on the cell culture dish. This can be achieved by using, for example, fixing of the cells by methanol or other fixatives or fixation agents known in the art, such as ethanol, acetone, formaldehyde or mixtures thereof or other fixation agents described herein. The analysis of the stability of, e.g., parental SiMa cells (human neuroblastoma cells; DSMZ no.: ACC 164) and iPS-derived neurons (Whitemarsh et al. (2012), Toxicol. Sci. 126, 426-35) using this fixation method did not reveal any differences between fresh and cell culture dishes stored seven days in the refrigerator.

As used herein, the singular forms “a”, “an” and “the” include both singular and plural reference unless the context clearly dictates otherwise. By way of example, “a cell” refers to one or more than one cell.

As used herein, the term “about” when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. Preferred is a range of plus or minus 10 percent.

The terms “comprising”, “comprises” and “comprised of” as used herein are synonymous with “including”, “includes” or “containing”, “contains”, and are inclusive or open-ended and do not exclude additional, non-recited members, elements or method steps. Evidently, the term “comprising” encompasses the term “consisting of”. More specifically, the term “comprise” as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase “consisting of” means that the composition (or device, or method) has the recited elements (or steps) and no more. In contrast, the term “comprises” can encompass also a method including further steps, e.g., steps d) and e), in addition to steps a), b) and c).

In case numerical ranges are used herein such as “in a concentration between 1 and 5 micromolar”, the range includes not only 1 and 5 micromolar, but also any numerical value in between 1 and 5 micromolar, for example, 2, 3 and 4 micromolar.

The term “in vitro” as used herein denotes outside, or external to, the animal or human body. The term “in vitro” as used herein should be understood to include “ex vivo”. The term “ex vivo” typically refers to tissues or cells removed from an animal or human body and maintained or propagated outside the body, e.g., in a culture vessel. The term “in vivo” as used herein denotes inside, or internal to, the animal or human body. Preferably, the method of the invention is an in vitro method.

The term “Neurotoxin polypeptide” as used herein denotes *Clostridium botulinum* and *Clostridium tetani* Neurotoxins, i.e. Botulinum toxins (BoNTs) and Tetanus toxin (TeNT). More specifically, said term means the BoNT/E Neurotoxin polypeptide or BoNT/E-MDM2 polypeptide if not stated otherwise. BoNT/E-MDM2 polypeptides and nucleic acid sequences encoding them have been defined and characterized in WO 2013/068476 the disclosure content of which is enclosed herewith by reference. Accordingly, the Neurotoxin polypeptide and, in particular, its light chain and heavy chain is derivable from BoNT/E. In an aspect, said light and heavy chain of the neurotoxin polypeptide are the light and heavy chain of a BoNT/E Neurotoxin. In another aspect, the polynucleotide encoding said Neurotoxin polypeptide comprises a nucleic acid sequence as shown in SEQ ID NO: 9 (nucleic acid sequence encoding BoNT/E), SEQ ID NO: 11 (nucleic acid sequence encoding a BoNT/E-MDM2 polypeptide) or SEQ ID NO: 13 (nucleic acid sequence encoding BoNT/E-MDM2 polypeptide). Moreover, encompassed is, in an aspect, a polynucleotide comprising a nucleic acid sequence encoding an amino acid sequence as shown in SEQ ID NO: 10 (BoNT/E), SEQ ID NO: 12 (BoNT/E-MDM2 polypeptide) or SEQ ID NO: 14 (BoNT/E-MDM2 polypeptide). Further encompassed is in an aspect of the means and methods of the present invention, a Neurotoxin polypeptide comprising or consisting of an amino acid sequence shown in SEQ ID NO: 10 (BoNT/E), SEQ ID NO: 12 (BoNT/E-MDM2 polypeptide) or SEQ ID NO: 14 (BoNT/E-MDM2 polypeptide). In a further aspect, the botulinum neurotoxin is a BoNT/E1 obtainable by using the codon-optimized nucleic acid sequence disclosed in WO 2014/068317.

In another aspect, the said polynucleotide is a variant of the aforementioned polynucleotide comprising one or more nucleotide substitutions, deletions and/or additions which in still another aspect may result in a polypeptide having one or more amino acid substitutions, deletions and/or additions. Moreover, a variant polynucleotide of the invention shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98% or at least 99% identical to the nucleic acid sequence as shown in SEQ ID NO: 9, 11 or 13, or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98% or at least 99% identical to the amino acid sequence as shown in SEQ ID NO: 10, SEQ ID NO: 12 or SEQ ID NO: 14. The term "identical" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. In an aspect, each of the aforementioned variant polynucleotides encodes a polypeptide retaining one or more and, in another aspect, all of the biological properties of the BoNT/E Neurotoxin polypeptide or the BoNT/E-MDM2 polypeptide. Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode BoNT/E Neurotoxins or BoNT/E-MDM2 polypeptides having improved or altered biological properties, e.g., they may comprise cleavage sites which are improved for enzyme recognition, may be improved for receptor binding, may have an altered, e.g., prolonged or reduced duration of biological activity, or any other property specified above.

Accordingly, the term "biological activity of a BoNT/E Neurotoxin polypeptide or a BoNT/E-MDM2 polypeptide" as used herein means the biological properties characteristic for a BoNT/E Neurotoxin polypeptide, namely, a) receptor binding, (b) internalization, (c) translocation across the endosomal membrane into the cytosol, and/or (d) endoproteolytic cleavage of proteins involved in synaptic vesicle membrane fusion. It is envisaged that the BoNT/E Neurotoxin polypeptide or BoNT/E-MDM2 polypeptide as used herein exhibits at least one of the properties a) to d) mentioned above, preferably endoproteolytic cleavage of proteins involved in synaptic vesicle membrane fusion, or two or three or all four biological properties listed in a) to d).

Aspects of the present disclosure comprise, in part, a cell from an established cell line. As used herein, the term "cell" refers to any eukaryotic cell susceptible to intoxication by a BoNT/E Neurotoxin polypeptide or BoNT/E-MDM2 polypeptide or any eukaryotic cell that can uptake a BoNT/E Neurotoxin polypeptide or BoNT/E-MDM2 polypeptide. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term "established cell line" is synonymous with "immortal cell line" or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. For example, primary neuronal cells can be used in the method of the invention. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a Neurotoxin polypeptide, such as BoNT/E, proteolytically cleaves a substrate, such as SNAP-25, and encompasses the binding of a Neurotoxin to a Neurotoxin receptor, such as BoNT/E to a BoNT/E receptor, the internalization of the neurotoxin/receptor complex, the translocation of the BoNT/E Neurotoxin light chain from an intracellular vesicle into the cytoplasm and the proteolytic cleavage of the BoNT/E Neurotoxin substrate SNAP-25. Alternatively, an established cell line can be one whose cells have had introduced from an exogenous source at least one component necessary for the cells to undergo the overall cellular mechanism whereby a Neurotoxin, such as BoNT/E, proteolytically cleaves a substrate, such as SNAP-25, and encompasses the binding of a Neurotoxin to a receptor, such as BoNT/E to a BoNT/E receptor, the internalization of the neurotoxin/receptor complex, the translocation of the BoNT/E Neurotoxin light chain from an intracellular vesicle into the cytoplasm and the proteolytic cleavage of the BoNT/E Neurotoxin substrate SNAP-25. Also referred to as a genetically-engineered cell line, cells from such an established cell line may, e.g., express an exogenous FGFR2, an exogenous FGFR3, an exogenous SV2, an exogenous Neurotoxin substrate SNAP-25, or any combination thereof.

The term "cell(s) susceptible to BoNT/E Neurotoxin intoxication" as denoted herein means a cell that can undergo the overall cellular mechanisms whereby a BoNT/E Neurotoxin polypeptide cleaves the BoNT/E Neurotoxin substrate SNAP-25 and encompasses the binding of the BoNT/E Neurotoxin to a BoNT/E receptor, the internalization of the Neurotoxin/receptor complex, the translocation of the BoNT/E Neurotoxin light chain from an intracellular vesicle into the cytoplasm and the proteolytic cleavage of the BoNT/E Neurotoxin substrate SNAP-25. Assays for determining the biological activity of BoNT/E Neurotoxin polypeptides are well known in the art and also described elsewhere herein; see, e.g., Pellett et al. (2011), Biochem. Biophys. Res. Commun. 404, 388-392; Whitemarsh et al. (2012), Toxicol. Sci. 126, 426-35. Accordingly, a "cell susceptible to BoNT/E Neurotoxin intoxication" as used herein means a BoNT/E Neurotoxin sensitive cell. The mentioned term comprises a cell or a cell line, for example, an isolated, primary cell or a cell line thereof or a cell of an established cell line or an established cell line, for example, tumor cells or tumor cell lines which are capable of differentiating to neuronal cells, such as neuroblastoma cells or neuroblastoma cell lines as defined elsewhere herein. For example, said neuroblastoma cell line can be a SiMa cell line which is commercially available from DSMZ (ACC 164). Specific clones of the cell line SiMa are furthermore disclosed in WO 2010/105234. Other neuroblastoma cell lines which can be used in the method of the invention can be obtained from ATCC or DSMZ, under the following ATCC or DSMZ numbers: Cell line N1E-115 under CRL-2263, cell line Neuro2a under CCL-131, cell line SH-SY5Y under CRL-2266, cell line PC12 under CRL-1721, cell line MHH-NB-11 under ACC 157 (DSMZ) and cell line SK-N-BE(2) under CRL-2271. Other tumor cells which are susceptible to Neurotoxin intoxication are P-19 cells (murine embryonal carcinoma cell line) (DSMZ no. ACC 316). Further encompassed by cells susceptible to BoNT/E Neurotoxin intoxication are induced pluripotent stem cell (iPS)-derived neurons, preferably human induced pluripotent stem cell (iPS)-derived neurons; see, e.g., Whitemarsh et al. (2012), loc. cit. Such human iPS-derived neurons are also commercially available, for instance, from Cellular Dynamics. Methods of generating iPS cells are described, for example, in Yu et al. (Science 2009 May 8; 324(5928): 797-801. Epub 2009), WO 2011/056971 and WO 2011/025852. In some aspects, iPS are differentiated into neurons using suitable methods, e.g., those described in WO 2012/135621 and U.S. Patent Applications US 2010/0279403 and US 2010/0216181.

The term "fixing the cells" or "fixation of cells" means fixing the cells using methods described in the art. Generally, fixation is a chemical process by which biological tissues are preserved from decay, thereby preventing autolysis. Fixation terminates any ongoing biochemical reactions, and may also increase the mechanical strength or stability of the treated tissues. Fixation preserves a sample of biological material such as a tissue or cells as close to its natural state as possible in the process of preparing said tissue or cells for examination or analysis. To this end, a fixative usually acts to disable intrinsic biomolecules—particularly proteolytic enzymes—which otherwise digests or damages the sample. Further, a fixative typically protects a sample from extrinsic damage. Fixatives are toxic to most common microorganisms including bacteria that might exist in a tissue or cell culture or which might otherwise colonize the fixed tissue or cell culture. In addition, many fixatives chemically alter the fixed material to make it less palatable either indigestible or toxic to opportunistic microorganisms. Finally, fixatives often alter the cells or tissues on a molecular level to increase their mechanical strength or stability. This increased strength and rigidity can help preserve the morphology such as shape and structure of the sample as it is processed for further analysis. It is evident to those skilled in the art that the choice of fixative and fixation protocol may depend on the additional processing steps and final analyses that are planned. For example, immunohistochemistry uses antibodies that bind specifically to a specific protein target, the antigen. Prolonged fixation can chemically mask these targets and prevent antibody binding. In these cases, for example, a quick fixation method using cold formalin can be used. Alternatively, the cells can be fixed by adding ice-cold methanol (−20° C.). Besides aldehydes such as formaldehyde or glutaraldehyde and alcohols such as ethanol or methanol, oxidizing agents, HEPES-glutamic acid buffer-mediated organic solvent protection effect (HOPE) fixative, acetone, or mixtures thereof, such as a mixture of methanol and acetone, methanol and ethanol, paraformaldehyde and Triton X-100, or paraformaldehyde and methanol, can be used in fixation protocols. In one aspect of the method of the invention, fixing the cells is carried out by the addition of a fixation agent selected from the group consisting of: methanol, ethanol, acetone, formaldehyde or mixtures thereof. To ensure and/or support free access of the antibody to its antigen, the cells can, optionally, be permeabilized by using an appropriate permeabilization buffer comprising at least one detergent, such as Triton X-100. A permeabilization buffer which can be used in the method of the invention is, e.g., 0.5% Triton X-100 in 10 mM PBS buffer. In other aspects of the methods of the invention, the cells can be permeabilized by using a permeabilization buffer such as PBS comprising at least one detergent selected from Tween 20, Saponin, Digitonin or n-Octyl-β-glucopyranoside. In other aspects, mixtures of two or more of the detergents mentioned herein can be used in the said permeabilization buffer. In general, fixation strengths and times are considerably shorter for cells than on the thicker, structurally complex tissue sections. For immunocytochemistry, sample preparation essentially entails fixing the target cells to the slide, cell culture dish or microtiter plate. Perfect fixation would immobilize the antigens, while retaining authentic cellular and subcellular architecture and permitting unhindered access of antibodies to all cells and subcellular compartments. Wide ranges of fixatives as exemplified above are commonly used, and the correct choice of method will depend on the nature of the antigen being examined and on the properties of the antibody used. Fixation methods fall generally into two classes: organic solvents and cross-linking reagents. Organic solvents such as alcohols and acetone remove lipids and dehydrate the cells, while precipitating the proteins on the cellular architecture. Cross-linking reagents such as paraformaldehyde form intermolecular bridges, normally through free amino groups, thus creating a network of linked antigens. Cross-linkers preserve cell structure better than organic solvents, but may reduce the antigenicity of some cell components, and often require the addition of a permeabilization step as indicated above, to allow access of the antibody to the specimen. Fixation with both methods may denature protein antigens, and for this reason, antibodies prepared against denatured proteins may be more useful for cell staining. The appropriate fixation method should be chosen according to the relevant application. Fixing methods of cells are well described in the art and thus known to those skilled in the art; see, e.g., Methods in cell biology, Volume 37: Antibodies in cell biology; Edited by David J. Asai; 1993, Academic Press Inc.

The term "contacting" as used in accordance with the method of the invention means bringing the cells and the respective antibodies in physical proximity as to allow physical and/or chemical interaction. Suitable conditions which allow for such specific interaction are well known to the person skilled in the art. Evidently, said conditions will depend on the antibodies and the cells to be applied in the method of the present invention and can be adapted routinely by the person skilled in the art. Moreover, a time being sufficient to allow interaction can also be determined by the skilled worker without further ado. It is to be understood that between the individual steps of contacting the cells and the respective antibodies recited in the method of the present invention, washing steps may be performed in order to obtain suitable conditions for contacting. For example, after contacting the cells with at least a first capture antibody specifically to the BoNT/E non-cleaved and BoNT/E-cleaved substrate SNAP-25 and with at least a second capture antibody specifically binding to the BoNT/E-cleaved substrate SNAP-25 in step c) of the method of the invention, a washing step can be incorporated to remove the remaining solution and/or excess first and second capture antibody, prior to applying the first detection antibody and/or second detection antibody. Similarly, after bringing the cells into contact with the first and/or second detection antibody in the method of the invention, a wash step can be included. An appropriate wash buffer is, for example, 10 mM PBS buffer (pH 7.4). More specifically, the term "contacting" used herein, refers to bringing the cells into contact with at least a first capture antibody specifically binding to the BoNT/E non-cleaved and BoNT/E-cleaved substrate SNAP-25 and with at least a second capture antibody specifically binding to BoNT/E-cleaved SNAP-25, under conditions which allow for binding of said capture antibodies to said SNAP-25, in step c) of the method of the invention. The first and second capture antibody can be applied to the cells simultaneously, for example, as a mixture, or subsequently. "Contacting" further refers to bringing into contact the cells with at least a first detection antibody specifically binding to the first capture antibody, under conditions which allow for binding of said first detection antibody to said first capture antibody, and at least a second detection antibody specifically binding to the second capture antibody, under conditions which allow for binding of said second detection antibody to said second capture antibody, in step d) of the method of the invention. Thereby, first and second detection complexes are being formed. Alternatively, the first and second detection antibodies can also be applied subsequently.

According to the method of the present invention, the "first capture antibody" specifically binds to an epitope comprised by the BoNT/E non-cleaved and BoNT/E-cleaved substrate SNAP-25. SNAP-25 is a known substrate of BoNT/E. Said first capture antibody allows for the determination of the total amount, i.e. complete content of SNAP-25 in the cells in that it specifically binds to an epitope available both in uncleaved SNAP-25 and in BoNT-E-cleaved SNAP-25. For BoNT/E, an epitope positioned N-terminally to the BoNT/E cleavage site (Arg (R) 180-Ile (I) 181), i.e. between amino acid residues 1 and 180 of SNAP-25 can be used for the first capture antibody.

In an aspect of the method of the invention, SNAP-25 is human SNAP-25A or B or a homolog, paralog or ortholog thereof from rat, mouse, bovine, *Danio, Carassius, Xenopus*, Torpedo, Strongylocentrotus, Loligo, Lymnaea, *Macaca mulatta* (Rhesus macaque), Pan troglodytes or Aplysia. The corresponding amino acid sequences of murine and human SNAP-25 are shown, e.g., in UniProt accession no. P60879 and P60880, respectively. SNAP-25 can be used as a naturally occurring, recombinant, exogenous or endogenous nucleic acid molecule or polypeptide. BoNT/E cleavage sites in the above-indicated SNAP-25 proteins are disclosed, for example, in EP 1 926 744 Bl.

Examples for appropriate antibodies which can be used as first capture antibodies in the method of the invention include, for example, the rabbit polyclonal anti-SNAP-25 antibody S9684 (Sigma) (Femindez-Salas E, Wang J, Molina Y, Nelson J B, Jacky B P S, et al. (2012) Botulinum Neurotoxin Serotype a Specific Cell-Based Potency Assay to Replace the Mouse Bioassay. PLoS ONE 7(11): e49516. doi:10.1371/journal.pone.0049516), the rabbit polyclonal anti-SNAP25 antibody PA5-19708 (Pierce Antibodies), the rabbit monoclonal anti-SNAP25 antibody ab108990 (Abcam), or the rabbit polyclonal anti-SNAP25 antibody PA5-19701 (Pierce Antibodies)

In another aspect of the method of the invention, the first capture antibody specifically binding to the BoNT/E non-cleaved and BoNT/E-cleaved substrate SNAP-25 can have an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$ or less than $1\times10^8$ $M^{-1}$ $s^{-1}$. In another aspect, the first capture antibody specifically binding to the BoNT/E non-cleaved and BoNT/E-cleaved substrate SNAP-25 can have an association rate constant of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$ or more than $1\times10^8$ $M^{-1}$ $s^{-1}$. In a further aspect, the first capture antibody specifically binding to the BoNT/E non-cleaved and BoNT/E-cleaved substrate SNAP-25 can have a dissociation rate constant of, e.g., less than $1\times10^3$ $s^{-1}$, less than $1\times10^{-4}$ $s^{-1}$, less than $1\times10^{-5}$ $s^{-1}$ or less than $1\times10^{-6}$ $s^{-1}$. In a still further aspect, the first capture antibody specifically binding to the BoNT/E non-cleaved and BoNT/E-cleaved substrate SNAP-25 can have a dissociation rate constant of, e.g., more than $1\times10^{-3}$ $s^{-1}$, more than $1\times10^{-4}$ $s^{-1}$, more than $1\times10^{-5}$ $s^{-1}$ or more than $1\times10^{-6}$ $s^{-1}$. As known in the art, the association rate constant is a constant used to characterize how quickly the antibody binds to its target. The dissociation rate constant is a constant used to characterize how quickly the antibody dissociates from its target.

In a further aspect, the first capture antibody is used for normalization of the BoNT/E-cleaved SNAP-25 in the cell.

In a further aspect of the method of the invention, the second capture antibody specifically binding to the BoNT/

E-cleaved SNAP-25 is a polyclonal or monoclonal antibody of the invention. Accordingly, the definitions and embodiments with respect to the antibody of the invention apply mutatis mutandis to the second capture antibody used in the method of the present invention. In another aspect of the method of the invention, the second capture antibody is a BoNT/E cleavage site-specific antibody as described in Jones et al., Journal of Immunological Methods 329 (2008), p. 92-101.

The term "first detection antibody" as used herein is an antibody specifically binding to the first capture antibody. Said first detection antibody allows for the specific detection of the first capture antibody. By measuring the amount of bound first detection antibody, the amount of first detection complexes can be determined since the amount of bound first detection antibody in the first detection complex correlates with the amount of first capture antibody (and accordingly the amount of total SNAP-25, i.e. BoNT/E-cleaved and non-cleaved SNAP-25) comprised by the first detection complex. For example, an appropriate species-specific antibody can be used as a first detection antibody: If a mouse antibody has been used as a first capture antibody, said first detection antibody can be an anti-mouse antibody specifically binding to the mouse antibody. The first detection antibody can be, for instance, an alkaline phosphatase (AP)-conjugated antibody, a horseradish-peroxidase (HRP)-conjugated antibody or an antibody conjugated to a fluorescence dye. Conjugation of enzymes to antibodies, for example, by using glutaraldehyde is well known in the art.

Enzyme linked immunosorbent assays (ELISA) have been used to quantitate a wide range of compounds and pathogens for almost 40 years. Initially, radioactivity was used to quantitate the assays, but radio-immunoassays (RIA) have been replaced with assays utilizing enzymes to obtain colorimetric results. Recently, new substrates have been developed to produce fluorescent and luminescent products. The basic tenet of the new assays remains the same as colorimetric assays: The substrate is converted into a measurable compound by the enzymatic activity of proteins conjugated to an antibody, which confers specificity.

Commonly used enzyme conjugates in ELISA are alkaline phosphatase or horseradish peroxidase. Accordingly, in one aspect, the first detection antibody can be, for instance, conjugated to alkaline phosphatase or horseradish peroxidase. Further examples of enzyme conjugates which can be used as a first detection antibody in the method of the invention include glucose oxidase which uses glucose as substrate, tyrosinase which converts the substrate 1-(4-Methyl-coumarin-7-yl)-3-(4-hydroxyphenyl)urea) (PAP-AMC) (Stratis Avrameas, Immunochemistry, Volume 6, Issue 1, January 1969, Pages 43-48, IN9-IN11, 49-52) or ß-galactosidase which converts the substrate 6,8-difluoro-4-methylumbelliferyl ß-d-galactopyranoside (DiFMUG) (Gee et al., Analytical Biochemistry, Volume 273, Issue 1, August 1999, pages 41-48). Upon addition of a substrate, said substrate is converted by the enzyme to a detectable form. For example, alkaline phosphatase catalyzes the cleavage of esters of phosphoric acid. If an alkaline phosphatase (AP)-conjugated antibody is used as a first detection antibody, an appropriate substrate such as a 4-methylumbelliferryl phosphate derivative, e.g., 6,8-Difluoro-4-methylumbelliferyl phosphate (DiFMUP), or fluorescein diphosphate (FDP). 6,8-difluoro-4-methylumbelliferyl phosphate (DiFMUP) is converted by the AP to a detectable form, i.e. the fluorogenic product 6,8-difluoro-4-methylumbelliferone. Said substrate is provided, e.g., by Molecular Probes. Fluorescence intensities of this reaction product of DiFMUP can be measured using excitation/emission maxima of about 358/450 nm. Further substrates which can be used for this purpose are 9H-(1,3-dichloro-9,9-dimethylacridin-2-one-7-yl) phosphate (DDAO-phosphate; Invitrogen), fluorescein diphosphate (FDP; Sigma Aldrich) or 4-methylumbelliferyl phosphate (MUP; Invitrogen). DDAO-phosphate is converted by the AP to the fluorogenic product dimethylacridinone (DDAO), having an excitation/emission maxima of about 646/659 nm. If FDP is used as substrate for the AP, the reaction product is fluorescein, having an excitation/emission maximum of about 490/514 nm. For MUP, the corresponding reaction product is 4-methylumbelliferone (7-hydroxy-4-methylcoumarin), having an excitation/emission maxima of about 360/449 nm. Also these substrates are commercially available, e.g. from Molecular Probes. Alternatively, horseradish peroxidase can be used as enzyme conjugate in the first detection antibody of the method of the invention. Horseradish peroxidase (HRP) catalyzes the reduction of hydrogen peroxide ($H_2O_2$) to water ($H_2O$). In the presence of specific substrates, which act as hydrogen donors, the action of HRP converts colorless or non-fluorescent molecules into colored and/or fluorescent moieties respectively. For instance, Amplex® Red (Life Technologies) is a substrate for use with HRP containing assays. Amplex Red, in the presence of peroxidase enzyme, reacts with $H_2O_2$ in a 1:1 stoichiometry to produce resorufin, a red fluorescent compound which has an absorption and fluorescence emission maxima of 563 nm and 587 nm, respectively. Another example for a HRP substrate is Amplex® UltraRed (Life Technologies). It has been reported that Amplex® UltraRed reagent (excitation/emission of ~570/585 nm) improves upon the performance of the Amplex® Red reagent, offering brighter fluorescence and enhanced sensitivity on a per-mole basis in horseradish peroxidase or horseradish peroxidase-coupled enzyme assays. Fluorescence of the oxidized Amplex® UltraRed reagent (Amplex® UltroxRed reagent) is also less sensitive to pH, and the substrate and its oxidation product exhibit greater stability that the Amplex® Red reagent in the presence of hydrogen peroxide ($H_2O_2$) or thiols such as dithiothreitol (DTT). Further appropriate HRP substrates which can be used in the method of the invention include, e.g., 10-Acetyl-3,7-Dihydroxyphenoxazine (ADHP; AnaSpec) or 3-(4-Hydroxyphenyl) propionic acid (HPPA; AnaSpec) (Tuuminen et al. 1991, J. Immunoassay 12, 29-46).

Alternatively, the first detection antibody can carry an appropriate, detectable label which allows for the detection of the first capture antibody. Labeling may be done by direct or indirect methods. Direct labeling involves binding of the label directly (covalently or non-covalently) to the first detection antibody. Indirect labeling involves binding (covalently or non-covalently) of an agent which specifically binds to the first detection antibody and which carries a detectable label. Such an agent may be, e.g., a secondary (higher order) antibody which specifically binds to the first detection antibody. The secondary antibody in such a case will be coupled to a detectable label. It will be understood that further higher order antibodies can be used in addition for detection of the first detection complex. The higher order antibodies are often used to increase the signal. Suitable higher order antibodies may also include the well-known streptavidin-biotin system (Vector Laboratories, Inc.), and the well-known Dako LSAB™2 and LSAB™+ (labeled streptavidin-biotin), or Dako PAP (Peroxidase Anti-Peroxidase). In a further aspect, the said label of the first detection antibody is a fluorescent dye, i.e. the first antibody is conjugated to a fluorescent dye. In this case, the fluorescence can be directly measured by a fluorescence reader. Typical fluorescent labels include fluorescent proteins such as GFP and its derivatives, Cy dyes such as Cy3, or Cy5, Texas Red, Fluorescein, and the Alexa dyes, e.g. Alexa 568.

The "second detection antibody" as used herein is an antibody specifically binding to the second capture antibody. The second detection antibody can be, for instance, conjugated to an enzyme such as alkaline phosphatase, horseradish peroxidase, glucose oxidase or tyrosinase. Accordingly, in one aspect, the second detection antibody is an alkaline phosphatase (AP)-conjugated antibody, a horseradish-peroxidase (HRP)-conjugated antibody, an glucose oxidase-conjugated antibody or a tyrosinase-conjugated antibody. Said second detection antibody allows for the specific detection of the second capture antibody. By measuring the amount of bound second detection antibody, the amount of second detection complexes can be determined since the amount of bound second detection antibody in the second detection complex correlates with the amount of second capture antibody (and accordingly the amount of BoNT/E-cleaved SNAP-25) comprised by the second detection complex. For example, if a mouse antibody has been used as a second capture antibody, an anti-mouse antibody can be used as a second detection antibody. The second detection antibody can carry an enzyme as set forth above or a label such as a fluorescent dye (i.e. the second detection antibody is conjugated to a fluorescent dye) as mentioned elsewhere herein with respect to the first detection antibody. In one aspect of the method of the invention, the enzyme conjugated to the first detection antibody differs from the enzyme conjugated to the second detection antibody in order to allow the specific detection of the respective first and second capture antibody in the method of the invention. For instance, if the first detection antibody is an AP-conjugated antibody, the second detection antibody can be a horseradish peroxidase (HRP)-conjugated antibody or vice versa. Further, the excitation/emission spectra of the fluorogenic substrates of the AP and HRP do not substantially overlap but differ from each other, i.e. they show a clear shift so as to allow the distinction of the fluorescence intensities generated by the respective product. For example, DiFMUP exhibits excitation/emission at ~358/450 nm, whereas Amplex UltraRed exhibits excitation/emission of ~570/585 nm, thereby allowing for accurate measurements of the fluorescence intensities generated by the conversion of said fluorogenic substrates by the respective enzyme. In a further aspect, the alkaline phosphatase (AP)-conjugated antibody is used as a first detection antibody for the antigen which is present in excess in the cell, i.e. for the measurement of the amount of the total (BoNT/E-cleaved and non-cleaved) SNAP-25, in the cell. The horseradish peroxidase (HRP)-conjugated antibody is used as a second detection antibody for the antigen which is present in the cell in a lower amount, i.e. for the measurement of the amount of the BoNT/E-cleaved SNAP-25, in the cell. As known in the art, HRP substrates are more sensitive than AP substrates meaning that lower amounts of analytes can be detected. If an HRP antibody is used as secondary antibody for the detection of BoNT/E-cleaved SNAP-25, lower amounts of BoNT/E-cleaved SNAP-25 are detectable. In turn, lower amounts of BoNT/E can be determined, thereby increasing the sensitivity of the assay. Because the AP antibody measures the total amount of SNAP-25 in the cell, high sensitivity for the substrate is not required, due to the excess of analyte.

The term "at least" as used herein such as, for example, "at least a first capture antibody" means that in addition to an antibody specifically binding to the non-cleaved and BoNT/E-cleaved substrate, one or more further antibodies with the mentioned specificity can be used in the method of the invention. Similarly, "at least a second capture antibody" means that in addition to an antibody of the invention specifically binding to the cleavage site of the BoNT/E-cleaved SNAP-25, one or more further antibodies with the mentioned specificity can be used in the method of the invention. Further, one or more first detection antibodies specifically binding to the first detection antibody (or first detection antibodies) can be used in the method of the invention. Similarly, one or more second detection antibodies specifically binding to the second detection antibody (or second detection antibodies) can be used in the method of the invention.

The term "first detection complex" refers to a complex comprising a first capture antibody and a first detection antibody which specifically binds to the non-cleaved and BoNT/E-cleaved SNAP-25, thereby allowing for the determination of the total content of SNAP-25 in the cell. The amount of first detection complex can be measured by determination of the amount of specifically bound first detection antibody. This can be achieved dependent on the nature of the enzyme or the label of the first detection antibody, e.g. by measuring the intensity of fluorescence.

The term "second detection complex" refers to a complex comprising the second capture antibody and the second detection antibody which specifically binds to the cleavage site of the BoNT/E-cleaved SNAP-25, thereby allowing for the determination of the content of BoNT/E-cleaved SNAP-25 in the cell. The amount of second detection complex can be measured by determination of the amount of specifically bound second detection antibody. This can be achieved dependent on the nature of the enzyme or the label of the second detection antibody, e.g. by measuring the intensity of fluorescence.

It is envisioned that instead of enzyme-linked immunosorbent analysis (ELISA), any detection system can be used to practice aspects of the method of the invention, with the provision that the signal to noise ratio can distinguish to a statistically significant degree the signal from the formed antibody-antigen complexes from the background signal. Non-limiting examples of immuno-based detection systems include immunoblot analysis, like Western blotting and dot-blotting, immunoprecipitation analysis, and sandwich ELISA. The detection of the signal can be achieved using autoradiography with imaging or phosphorimaging (AU), bioluminescence (BL), fluorescence, resonance energy transfer, plane polarization, colormetric, or flow cytometry (FC). Descriptions of immuno-based detection systems are disclosed, for example, in Commonly Used Techniques in Molecular Cloning, pp. A8.1-A8-55 (Sambrook & Russell, eds., Molecular Cloning A Laboratory Manual, Vol. 3, 3.sup.rd ed. 2001); Detection Systems, pp. A9.1-A9-49 (Sambrook & Russell, eds., Molecular Cloning A Laboratory Manual, Vol. 3, 3.sup.rd ed. 2001).

In one aspect of the method of the invention, the method is a fluorescence method.

In a further aspect, the cells, antibodies such as the antibody of the invention, Neurotoxin polypeptides such as BoNT/E and Neurotoxin substrates such as SNAP-25 or any other product as referred to herein are isolated cells, antibodies, Neurotoxin polypeptides, Neurotoxin substrates or products, respectively. As used herein, the term "isolated" such as an isolated antibody refers to a molecule separated from its natural environment by the use of human intervention.

In one aspect of the method of the invention, the BoNT/E Neurotoxin polypeptide comprises an amino acid sequence selected from the group consisting of:

a) an amino acid sequence as shown in SEQ ID NO: 10, SEQ ID NO: 12 or SEQ ID NO: 14; and
b) an amino acid sequence which has at least 50%, 60%, 70%, 75%, 80%, 85%, 90%, 95%, 96%, 97%, 98%, 99% or 100% sequence identity to the amino acid sequence as shown in SEQ ID NO: 10, SEQ ID NO: 12 or SEQ ID NO: 14.

In a further aspect of the method of the invention, the cells are neuronal cells or neuronal differentiated cells selected from the group consisting of: primary neuronal cells, tumor cells which are capable of differentiating to neuronal cells such as neuroblastoma cells, P19 cells or induced pluripotent stem cell (IPS)-derived neurons.

In a still further aspect of the method of the invention, fixing the cells is carried out by the addition of a fixation agent selected from the group consisting of: methanol, ethanol, acetone, formaldehyde or mixtures thereof.

In another aspect of the method of the invention, said first capture antibody specifically binding to the non-cleaved and BoNT/E-cleaved substrate is the rabbit polyclonal anti-SNAP-25 antibody S9684, the rabbit polyclonal anti-SNAP25 antibody PA5-19708 (Pierce Antibodies), the rabbit monoclonal anti-SNAP25 antibody ab108990 (Abcam) or the rabbit polyclonal anti-SNAP25 antibody PA5-19701 (Pierce Antibodies).

In one aspect of the method of the invention, the first detection antibody is an alkaline phosphatase (AP)-conjugated antibody, a horseradish-peroxidase (HRP)-conjugated antibody or an antibody conjugated to a fluorescence dye.

In one aspect of the method of the invention, the second detection antibody is an alkaline phosphatase (AP)-conjugated antibody, a horseradish-peroxidase (HRP)-conjugated antibody, a glucose oxidase-conjugated antibody, a tyrosinase-conjugated antibody or a β-Galactosidase antibody. Preferably, the second detection antibody is different from the first detection antibody.

In a further aspect of the method of the invention, the HRP substrate is Amplex UltraRed, 10-Acetyl-3,7-Dihydroxyphenoxazine (ADHP) or 3-(4-Hydroxyphenyl) propionic acid (HPPA).

In a still further aspect of the method of the invention, wherein the AP substrate is a 4-methylumbelliferyl phosphate derivative such as 6,8-Difluoro-4-methylumbelliferyl phosphate (DiFMUP), or fluorescein diphosphate (FDP).

The invention also pertains to a kit for carrying out the method of the invention, comprising:

a) an arrangement of a first capture antibody, a second capture antibody which is preferably a polyclonal or monoclonal antibody of the invention, a first detection antibody and a second detection antibody, wherein said arrangement allows for carrying out the methods of the invention;
b) means for calculating the amount of SNAP-25 cleaved by BoNT/E based on the amount of the second detection complexes determined by the arrangement according to a); and
c) instructions for carrying out said method of the invention.

The term "kit" as used herein refers to a collection of the aforementioned means or reagents of the present invention which may or may not be packaged together. The components of the kit may be comprised by separate vials (i.e. as a kit of separate parts) or provided in a single vial. Moreover, it is to be understood that the kit of the present invention is to be used for practicing the method referred to herein above. In one aspect, it is envisaged that all components are provided in a ready-to-use manner for practicing the method referred to herein. In a further aspect, the kit contains instructions for carrying out the said method. The instructions can be provided by a user manual in paper- or electronic form. For example, the manual may comprise instructions for interpreting the results obtained when carrying out the aforementioned methods using the kit of the present invention.

Finally, the invention relates in another aspect to a method for manufacture of a formulated BoNT/E Neurotoxin product or BoNT/E-MDM2 Neurotoxin product for use in pharmaceutical or cosmetic applications, comprising (i) determining the biological activity of a BoNT/E Neurotoxin or BoNT/E-MDM2 Neurotoxin polypeptide by the method of the invention and (ii) formulating the BoNT/E Neurotoxin or BoNT/E-MDM2 Neurotoxin polypeptide for use in pharmaceutical or cosmetic applications so that a formulated BoNT/E Neurotoxin product or BoNT/E-MDM2 Neurotoxin product is being obtained. The BoNT/E Neurotoxin or BoNT/E-MDM2 Neurotoxin polypeptide can be formulated to a BoNT/E Neurotoxin product or BoNT/E-MDM2 Neurotoxin product by various techniques dependent on the desired application purposes which are known in the art. For example, the (biologically active) BoNT/E Neurotoxin polypeptide can be used in combination with one or more pharmaceutically acceptable carriers as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pennsylvania. In an aspect, the pharmaceutical composition can be dissolved in a diluent, prior to administration. The diluent is also selected so as not to affect the biological activity of the BoNT/E or BoNT/E-MDM2 Neurotoxin polypeptide. Examples of such diluents are distilled water or physiological saline. In addition, the pharmaceutical composition or formulation may also include other carriers or non-toxic, non-therapeutic, non-immunogenic stabilizers and the like. Thus, the formulated BoNT/E Neurotoxin product or BoNT/E-MDM2 Neurotoxin product can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208. In one aspect, the biological activity determined according to step (i) by the method of the invention corresponds to a BoNT/E Neurotoxin or BoNT/E-MDM2 Neurotoxin polypeptide activity of 25, 50, 75, 100, 125, 150 or 200 U (Mouse LD50 units). The formulated BoNT/E Neurotoxin product or BoNT/E-MDM2 Neurotoxin product may be used for human or animal therapy of various diseases or disorders in a therapeutically effective dose or for cosmetic purposes.

The disease or disorder as referred to herein is selected from the group consisting of voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, masseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinson's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, myelon tumor and vaginism. A cosmetic use is selected from treatment or reduction of wrinkles like crow's feet or GFL, frowning, facial asymmetries.

All references cited in this specification are herewith incorporated by reference with respect to their entire disclosure content and the disclosure content specifically mentioned in this specification.

The FIGURE shows:

FIG. 1: Diagram representing the mode of action of the cell-based assay of the invention. Cells susceptible to BoNT/E intoxication are seeded in multiwell plates, Thereafter, the cells are intoxicated with BoNT/E and after a given intoxication period the cells are fixated. The specific antibody for BoNT/E-cleaved SNAP-25 and the specific antibody for uncleaved SNAP-25 bind to the specific binding sites on SNAP-25. Using enzyme-coupled anti-host specific secondary antibodies, these binding events can be used to generate measurable signals which correlate with the concentration of BoNT/E-cleaved SNAP-25 and the total amount of SNAP-25 within the well. With increasing BoNT/E concentration, the amount of measured cleaved SNAP-25 increases resulting in a gain of signal.

The invention will now be illustrated by the following Examples which shall, however, not be construed as limiting the scope of the present invention.

EXAMPLE 1: GENERATION OF MONOCLONAL ANTIBODIES SPECIFICALLY BINDING TO THE CLEAVAGE SITE OF THE BoNT/E-CLEAVED SUBSTRATE SNAP-25

Mouse monoclonal antibodies specifically binding to the cleavage site of the BoNT/E-cleaved substrate SNAP-25 have been generated using the hybridoma standard technique. To this end, Balb/c mice (female, 8 weeks) have been immunized with the peptide "C-NEIDTQNRQIDR-OH" (SEQ ID NO: 1). The N-terminal Cysteine residue is not derived from the SNAP-25 amino acid sequence but has been introduced for linking the peptide to the keyhole limpet hemocyanin (KLH). Hybridoma cells have been obtained by the fusion of mouse spleen cells with the myeloma cell line SP2/0-Ag14 (SP2/0) purchased from the German Collection of Microorganisms and Cell Culture (DSMZ GmbH, Braunschweig, ACC 146); see also Hemmerlein et al., Molecular Cancer 2006, 5, 41. Antibodies specifically binding to the cleavage site of the BoNT/E-cleaved substrate SNAP-25 were screened in ELISA. The obtained clones have been selected with respect to their specificity and affinity to BoNT/E-cleaved SNAP-25. As a negative control, the clones have been tested for their non-binding to non-cleaved SNAP-25$_{206}$. As a result, the mouse monoclonal antibody produced by hybridoma pCNEI 32-7-1, 3614-000 was found to be highly specific for BoNT/E-cleaved SNAP-25, with no detectable cross-reactivity to SNAP25$_{206}$ in ELISA and Western blots.

The hybridoma cell line pCNEI 32-7-1, 3614-000 producing the monoclonal antibody of the invention specifically binding to BoNT/E-cleaved SNAP-25 has been deposited by the Applicant under the Budapest Treaty on Dec. 17, 2014, at DSMZ—Deutsche Sammlung von Mikroorganismen und Zellkulturen GmbH, Inhoffenstraße 7 B, 38124 Braunschweig, Germany under accession number DSM ACC3261. The amino acid sequences of CDR-H1, CDR-H2 and CDR-H3 of this monoclonal antibody are shown in SEQ ID NOs. 18, 19 and 20, respectively. The amino acid sequences of CDR-L1, CDR-L2 and CDR-L3 of this monoclonal antibody are shown in SEQ ID Nos. 15, 16 and 17, respectively. The amino acid sequence of the VH region of this monoclonal antibody is depicted in SEQ ID NO. 22, and the amino acid sequence of the VL region of this monoclonal antibody is shown in SEQ ID NO. 21.

EXAMPLE 2: DOUBLE-FLUORESCENCE-CB-BoNT/E ACTIVITY ELISA

Fixation of Cells

1. Remove the media/toxin solution. Add 100 μl/well ice-cold methanol (−20° C.) and incubate for 20 min at −20° C.

Note: Perform all subsequent steps at room temperature.

After Cell Fixation:

1. Remove the methanol solution and add 100 μl/well PBS buffer. For longer storage (>1 day) one should add 300 μl/well PBS buffer and seal the plates with parafilm. The plates should be stored in the refrigerator.
2. Remove the PBS Buffer and wash the cells 3 times with 300 μl/well of PBS buffer. Each step should be performed for 1 minute with gentle shaking.
3. Remove the PBS buffer and add 100 μl/well of quenching buffer and incubate for 20 minutes with gentle shaking.
4. Remove the quenching buffer and wash the cells once with 300 μl/well of PBS buffer for 3 minutes under gentle shaking.
5. Remove the PBS buffer, and add 200 μl/well of blocking buffer and incubate for 1 hour with gentle shaking.
6. Remove the blocking buffer and add 100 μl of the primary antibody mixture (antibody dilution in blocking buffer) to each well. Incubate overnight (16-18 h) with gentle shaking. The cells are simultaneously incubated with two primary antibodies: a mouse antibody specific for the BoNT/E-cleaved SNAP25 and a polyclonal rabbit antibody that recognizes SNAP-25 (antibody for determining the total amount of SNAP-25 for normalization).
7. Remove the primary antibody mixture and wash the cells 4 times with 300 μl of PBS buffer. Each step should be performed for 3 minutes with gentle shaking.
9. Remove the PBS buffer, and add 100 μl of the secondary antibody mixture: HRP-conjugated anti-mouse and AP-conjugated anti-rabbit secondary antibodies (antibody dilution in blocking buffer) to each well and incubate for 2.5-3 hours with gentle shaking.
10. Remove the secondary antibody mixture and wash the cells 6 times with 300 μl/well of HEPES buffer. Each wash step should be performed for 3 minutes with gentle shaking.
11. Remove the HEPES buffer from the plate and add 75 μl of a fluorogenic substrate for horseradish-peroxidase (HRP substrate) to each well. Incubate for 50 minutes with gentle shaking. Protect the plates from direct light.
12. Add 75 μl of a fluorogenic substrate for alkaline phosphatase (AP substrate) to each well and incubate for an additional 50 minutes at with gentle shaking. Protect the plates from direct light.

13. Read the plates using a fluorescence plate reader:
excitation at 540 nm; emission at 600 nm.
excitation at 360 nm; emission at 450 nm.

15. Calculation

For normalization, the RFU value for BoNT/E-cleaved SNAP-25 (fluorescence at 600 nm) is normalized to RFU of total SNAP-25 (450 nm) in each well. For better illustration of RFUs in a diagram all values are multiplied with a factor 1000 using the following equation:

$$\frac{RFU\ (600\ \text{nm})}{RFU\ (450\ \text{nm})} \times 1000$$

Subsequently the resulting RFU values are averaged for each standard or sample.

Reagent Preparation

PBS Buffer (10 mM):
Phosphate buffered saline (Sigma, #P5368) (pH 7.4)

Quenching buffer:
0.6% $H_2O_2$ in 10 mM PBS buffer (pH 7.4)

Blocking buffer:
2% BSA in 10 mM PBS buffer (pH 7.4)

HEPES buffer:
50 mM HEPES (pH 7.4)

HRP substrate:
50 mM HEPES (pH 7.4)
0.007% $H_2O_2$
150 μM Amplex UltraRed

AP substrate:
25 mM Diethanolamine (pH 9.8)
2 mM $MgCl_2$
100 μM DiFMUP

The invention claimed is:

1. A monoclonal antibody comprising the complementarity determining regions (CDRs) of CDR-L1 (SEQ ID NO. 15), CDR-L2 (SEQ ID NO. 16), CDR-L3 (SEQ ID NO. 17), CDR-H1 (SEQ ID NO. 18), CDR-H2 (SEQ ID NO. 19) and CDR-H3 (SEQ ID NO. 20), wherein the monoclonal antibody specifically binds to Botulinum toxin E-(BoNT/E) cleaved synaptosomal-associated protein of 25 kDa (SNAP-25).

2. The or monoclonal antibody of claim 1, wherein the antibody specifically binds an epitope consisting of the amino acid sequence of SEQ ID NO: 2 (NEIDTQNRQIDR).

3. The monoclonal antibody of claim 1, wherein the antibody is produced by hybridoma cell line pCNEI 32-7-1, 3614-000 deposited on Dec. 17, 2014, at DSMZ—Deutsche Sammlung von Mikroorganismen and Zellkulturen GmbH, Inhoffenstraße 7 B, 38124 Braunschweig, Germany, under the accession number DSM ACC3261.

4. The monoclonal antibody of claim 1, wherein the antibody comprises the VH region (SEQ ID NO. 22) and the VL region (SEQ ID NO. 21).

* * * * *